United States Patent
Milsom et al.

(10) Patent No.: US 10,874,285 B2
(45) Date of Patent: Dec. 29, 2020

(54) METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

(71) Applicant: Cornell University, New York, NY (US)

(72) Inventors: Jeffrey Milsom, New York, NY (US); Howard Riina, Scarsdale, NY (US); J. Frederick Cornhill, New York, NY (US); Edward Dickinson, Littleton, MA (US); Clair Strohl, Norfolk, MA (US); James J. Mahoney, Jr., Hyde Park, MA (US); Pat Coppola, Bedford, MA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/936,833

(22) Filed: Mar. 27, 2018

(65) Prior Publication Data
US 2019/0069761 A1    Mar. 7, 2019

Related U.S. Application Data

(63) Continuation of application No. 14/540,355, filed on Nov. 13, 2014, now Pat. No. 9,924,853, which is a
(Continued)

(51) Int. Cl.
*A61B 1/00* (2006.01)
*A61B 1/31* (2006.01)

(52) U.S. Cl.
CPC ...... *A61B 1/00082* (2013.01); *A61B 1/00135* (2013.01); *A61B 1/31* (2013.01)

(58) Field of Classification Search
CPC .......... A61M 25/1011; A61M 25/1018; A61M 2025/1015; A61M 2025/1013;
(Continued)

(56) References Cited

U.S. PATENT DOCUMENTS

| 2,473,742 A | 6/1949 | Auzin |
| 4,066,071 A | 1/1978 | Nagel |

(Continued)

FOREIGN PATENT DOCUMENTS

| AU | 2012 203 616 A1 | 7/2012 |
| CA | 2988249 | 12/2016 |

(Continued)

*Primary Examiner* — Katrina M Stransky
(74) *Attorney, Agent, or Firm* — Pandiscio & Pandiscio

(57) ABSTRACT

The present invention comprises the provision and use of a novel endoscopic device which is capable of stabilizing, straightening, expanding and/or flattening the side wall of a body lumen and/or body cavity so as to better present the side wall tissue for examination and/or treatment during an endoscopic procedure. The present invention also comprises the provision and use of a novel endoscopic device capable of steadying and/or stabilizing the distal tips and/or working ends of instruments inserted into a body lumen and/or body cavity, whereby to facilitate the use of those instruments.

8 Claims, 37 Drawing Sheets

Related U.S. Application Data continuation of application No. 12/969,059, filed on Dec. 15, 2010, now Pat. No. 8,979,884.

(60) Provisional application No. 61/284,215, filed on Dec. 15, 2009.

(58) Field of Classification Search
CPC ....... A61M 2025/1052; A61B 1/00135; A61B 1/00154; A61B 1/00082; A61B 17/12136; A61B 17/1204
See application file for complete search history.

(56) References Cited

U.S. PATENT DOCUMENTS

| | | | |
|---|---|---|---|
| 4,198,981 | A | 4/1980 | Sinnreich |
| 4,224,929 | A | 9/1980 | Furihata |
| 4,445,892 | A | 5/1984 | Hussein et al. |
| 4,862,874 | A | 9/1989 | Kellner |
| 5,025,778 | A | 6/1991 | Silverstein et al. |
| 5,078,731 | A | 1/1992 | Hayhurst |
| 5,105,800 | A | 4/1992 | Takahashi et al. |
| 5,147,382 | A | 9/1992 | Gertzman et al. |
| 5,197,971 | A | 3/1993 | Bonutti |
| 5,217,001 | A | 6/1993 | Nakao et al. |
| 5,423,821 | A | 6/1995 | Pasque |
| 5,662,587 | A | 9/1997 | Grundfest et al. |
| 5,718,680 | A | 2/1998 | Kraus et al. |
| 5,762,604 | A | 6/1998 | Kieturakis |
| 5,833,650 | A | 11/1998 | Imran |
| 5,938,585 | A | 8/1999 | Donofrio |
| 5,954,731 | A | 9/1999 | Yoon |
| 6,007,482 | A | 12/1999 | Madni et al. |
| 6,007,483 | A | 12/1999 | Kieturakis |
| 6,071,273 | A | 6/2000 | Euteneuer et al. |
| 6,139,517 | A | 10/2000 | Macoviak et al. |
| 6,234,958 | B1 | 5/2001 | Snoke et al. |
| 6,277,065 | B1 | 8/2001 | Donofrio |
| 6,309,346 | B1 | 10/2001 | Farhadi |
| 6,375,665 | B1 | 4/2002 | Nash et al. |
| 6,475,226 | B1 | 11/2002 | Belef et al. |
| 6,575,932 | B1 | 6/2003 | O'Brien et al. |
| 6,585,639 | B1 | 7/2003 | Kotmel et al. |
| 6,741,884 | B1 | 5/2004 | Freeman et al. |
| 6,764,441 | B2 | 7/2004 | Chiel et al. |
| 6,790,173 | B2 | 9/2004 | Saadat et al. |
| 6,793,661 | B2 | 9/2004 | Hamilton et al. |
| 6,929,601 | B2 | 8/2005 | Nakao |
| 6,951,554 | B2 | 10/2005 | Johansen et al. |
| 6,988,986 | B2 | 1/2006 | Gross |
| 7,041,051 | B2 | 5/2006 | Bernstein |
| 7,410,483 | B2 | 8/2008 | Danitz et al. |
| 7,510,523 | B2 | 3/2009 | Sakamoto |
| 7,591,782 | B2 | 9/2009 | Fujikura |
| 7,635,346 | B2 | 12/2009 | Cabiri et al. |
| 7,678,044 | B2 | 3/2010 | Fujikura |
| 7,699,771 | B2 | 4/2010 | Wendlandt |
| 7,708,687 | B2 | 5/2010 | Bern et al. |
| 7,798,992 | B2 | 9/2010 | Ortiz |
| 7,833,150 | B2 | 11/2010 | Yamamoto et al. |
| 7,901,347 | B2 | 3/2011 | Sekiguchi et al. |
| 7,909,755 | B2 | 3/2011 | Itoi |
| 7,935,047 | B2 | 5/2011 | Yoshida et al. |
| 7,959,559 | B2 | 6/2011 | Yamaya |
| 7,963,911 | B2 | 6/2011 | Turliuc |
| 8,012,084 | B2 | 9/2011 | Machida |
| 8,092,372 | B2 | 1/2012 | Machida |
| 8,096,942 | B2 | 1/2012 | Yoshida et al. |
| 8,109,903 | B2 | 2/2012 | Terliuc et al. |
| 8,147,401 | B2 | 4/2012 | Yamaya |
| 8,187,173 | B2 | 5/2012 | Miyoshi |
| 8,337,395 | B2 | 12/2012 | Suzuki et al. |
| 8,403,827 | B2 | 3/2013 | Matsui et al. |
| 8,439,825 | B2 | 5/2013 | Sekiguchi |
| 8,460,179 | B2 | 6/2013 | Ikeda et al. |
| 8,506,479 | B2 | 8/2013 | Piskun et al. |
| 8,523,763 | B2 | 9/2013 | Sinai et al. |
| 8,679,001 | B2 | 3/2014 | Sinai et al. |
| 8,932,211 | B2 | 1/2015 | Piskun et al. |
| 8,979,884 | B2 | 3/2015 | Milsom et al. |
| 9,125,636 | B2 | 9/2015 | Piskun et al. |
| 9,161,746 | B2 | 10/2015 | Piskun et al. |
| 9,186,130 | B2 | 11/2015 | Piskun et al. |
| 9,186,131 | B2 | 11/2015 | Piskun et al. |
| 9,554,690 | B2 | 1/2017 | Piskun et al. |
| 9,565,998 | B2 | 2/2017 | Piskun et al. |
| 9,655,506 | B2 | 5/2017 | Piskun et al. |
| 9,713,416 | B2 | 7/2017 | Piskun et al. |
| 9,737,194 | B2 | 8/2017 | Piskun et al. |
| 9,986,893 | B2 | 6/2018 | Cornhill et al. |
| 2002/0013601 | A1 | 1/2002 | Nobles et al. |
| 2002/0120180 | A1 | 8/2002 | Speier et al. |
| 2003/0225433 | A1 | 12/2003 | Nakao |
| 2004/0102681 | A1 | 5/2004 | Gross |
| 2004/0186349 | A1 | 9/2004 | Ewers et al. |
| 2004/0210116 | A1 | 10/2004 | Nakao |
| 2004/0260150 | A1 | 12/2004 | Bernstein |
| 2004/0260333 | A1 | 12/2004 | Dubrul et al. |
| 2005/0033363 | A1 | 2/2005 | Bojarski et al. |
| 2005/0033401 | A1 | 2/2005 | Cunniffe et al. |
| 2005/0107664 | A1 | 5/2005 | Kalloo et al. |
| 2005/0165432 | A1 | 7/2005 | Heinrich |
| 2005/0215855 | A1 | 9/2005 | Machida |
| 2005/0277809 | A1 | 12/2005 | Takano et al. |
| 2006/0106288 | A1 | 5/2006 | Roth et al. |
| 2006/0161044 | A1 | 7/2006 | Oneda et al. |
| 2006/0183974 | A1 | 8/2006 | Levy et al. |
| 2006/0189845 | A1 | 8/2006 | Maahs et al. |
| 2006/0241345 | A1 | 10/2006 | Oishi et al. |
| 2006/0258972 | A1 | 11/2006 | Mangiardi et al. |
| 2007/0049797 | A1 | 3/2007 | Yoshida et al. |
| 2007/0106302 | A1 | 5/2007 | Ortiz |
| 2007/0142706 | A1 | 6/2007 | Matsui et al. |
| 2007/0167682 | A1 | 7/2007 | Goldfarb et al. |
| 2007/0215162 | A1 | 9/2007 | Glassenberg et al. |
| 2007/0244361 | A1 | 10/2007 | Ikeda et al. |
| 2007/0265499 | A1 | 11/2007 | Wood |
| 2007/0276181 | A1 | 11/2007 | Terliuc |
| 2007/0282166 | A1 | 12/2007 | Ayala et al. |
| 2008/0065116 | A1 | 3/2008 | Lee et al. |
| 2008/0086155 | A1 | 4/2008 | Rothe et al. |
| 2008/0091063 | A1 | 4/2008 | Terliuc |
| 2008/0091068 | A1 | 4/2008 | Terliuc |
| 2008/0161645 | A1 | 7/2008 | Goldwasser et al. |
| 2008/0200756 | A1 | 8/2008 | Okada et al. |
| 2008/0249358 | A1 | 10/2008 | Motai et al. |
| 2009/0156896 | A1 | 6/2009 | Kura |
| 2009/0156996 | A1 | 6/2009 | Milsom et al. |
| 2009/0187069 | A1 | 7/2009 | Terliuc et al. |
| 2009/0203995 | A1 | 8/2009 | Matonick |
| 2009/0227835 | A1* | 9/2009 | Terliuc ............... A61B 1/00082 600/106 |
| 2009/0234188 | A1 | 9/2009 | Matsuura |
| 2009/0287051 | A1 | 11/2009 | Itoi |
| 2009/0287058 | A1 | 11/2009 | Terliuc |
| 2010/0010530 | A1 | 1/2010 | Rhee |
| 2010/0049162 | A1 | 2/2010 | Hameed |
| 2010/0105983 | A1 | 4/2010 | Oneda et al. |
| 2010/0168510 | A1 | 7/2010 | Rogers et al. |
| 2010/0217078 | A1 | 8/2010 | Yamakawa et al. |
| 2010/0217185 | A1 | 8/2010 | Terliuc et al. |
| 2011/0009863 | A1 | 1/2011 | Marczyk et al. |
| 2011/0054253 | A1 | 3/2011 | Albiñana et al. |
| 2011/0092770 | A1 | 4/2011 | Matsui et al. |
| 2011/0092963 | A1 | 4/2011 | Castro |
| 2011/0112410 | A1 | 5/2011 | Hirota |
| 2011/0160536 | A1 | 6/2011 | Blum |
| 2011/0172491 | A1 | 7/2011 | Piskun et al. |
| 2011/0190583 | A1 | 8/2011 | Ashida et al. |
| 2011/0245858 | A1 | 10/2011 | Milsom et al. |
| 2011/0251555 | A1 | 10/2011 | Ducharme et al. |
| 2012/0130170 | A1 | 5/2012 | Terliuc |
| 2012/0136343 | A1 | 5/2012 | Burnett |
| 2012/0150210 | A1 | 6/2012 | Fan et al. |

(56) References Cited

U.S. PATENT DOCUMENTS

| | | |
|---|---|---|
| 2012/0157771 A1 | 6/2012 | Avitsian et al. |
| 2012/0178994 A1 | 7/2012 | Schembre |
| 2012/0232347 A1 | 9/2012 | Fujikura et al. |
| 2013/0116549 A1 | 5/2013 | Gunday et al. |
| 2013/0144118 A1 | 6/2013 | Piskun et al. |
| 2013/0165942 A1 | 6/2013 | Tan-Malecki et al. |
| 2013/0217957 A1 | 8/2013 | Maahs et al. |
| 2013/0267936 A1 | 10/2013 | Stroup et al. |
| 2013/0345519 A1 | 12/2013 | Piskun et al. |
| 2014/0188159 A1 | 7/2014 | Steege |
| 2015/0018616 A1 | 1/2015 | Kumoyama |
| 2015/0133774 A1 | 5/2015 | Milsom et al. |
| 2015/0150436 A1 | 6/2015 | Cornhill et al. |
| 2015/0157192 A1 | 6/2015 | Piskun et al. |
| 2015/0164524 A1 | 6/2015 | Malkowski et al. |
| 2015/0209024 A1 | 7/2015 | Piskun et al. |
| 2015/0265818 A1 | 9/2015 | Piskun et al. |
| 2015/0272564 A1 | 10/2015 | Piskun et al. |
| 2015/0282800 A1 | 10/2015 | Piskun et al. |
| 2015/0297209 A1 | 10/2015 | Piskun et al. |
| 2015/0313584 A1 | 11/2015 | Piskun et al. |
| 2015/0335229 A1 | 11/2015 | Terliuc |
| 2016/0015252 A1 | 1/2016 | Piskun et al. |
| 2016/0029875 A1 | 2/2016 | Okada |
| 2016/0089002 A1 | 3/2016 | Burton et al. |
| 2016/0278626 A1 | 9/2016 | Cornhill et al. |
| 2016/0278757 A1 | 9/2016 | Piskun et al. |
| 2016/0309996 A1 | 10/2016 | Piskun et al. |
| 2016/0310124 A1 | 10/2016 | Piskun et al. |
| 2016/0338572 A1 | 11/2016 | Piskun et al. |
| 2016/0374658 A1 | 12/2016 | Piskun |
| 2017/0079636 A1 | 3/2017 | Piskun et al. |
| 2017/0105726 A1 | 4/2017 | Smith et al. |
| 2017/0135567 A1 | 5/2017 | Piskun et al. |
| 2018/0035872 A1 | 2/2018 | Cruz et al. |

FOREIGN PATENT DOCUMENTS

| | | |
|---|---|---|
| CN | 1647747 A | 8/2005 |
| CN | 105832279 | 8/2016 |
| EP | 0 402 467 | 12/1990 |
| EP | 1 654 977 | 5/2006 |
| EP | 1 782 726 | 5/2007 |
| EP | 2 026 866 | 2/2009 |
| EP | 1 977 679 | 8/2010 |
| EP | 1 731 084 | 12/2010 |
| EP | 2 364 637 | 9/2011 |
| EP | 1 718 193 | 7/2013 |
| JP | 3-258268 | 11/1991 |
| JP | 6-113998 | 4/1994 |
| JP | 7-308388 | 11/1995 |
| JP | 2000-033071 | 2/2000 |
| JP | 2000-037347 | 2/2000 |
| JP | 2004-016728 | 1/2004 |
| JP | 2007-296054 | 11/2007 |
| JP | 2011-087647 | 5/2011 |
| JP | 2012-029886 | 2/2012 |
| WO | WO 1989/007413 | 8/1989 |
| WO | WO 2001/054568 | 8/2001 |
| WO | WO 2002/087495 | 11/2002 |
| WO | WO 2003/103517 | 12/2003 |
| WO | WO 2004/060463 | 7/2004 |
| WO | WO 2005/074377 | 8/2005 |
| WO | WO 2005/089627 | 9/2005 |
| WO | WO 2005/110204 | 11/2005 |
| WO | WO 2006/138013 | 12/2006 |
| WO | WO 2007/017854 | 2/2007 |
| WO | WO 2007/135665 | 11/2007 |
| WO | WO 2008/004228 | 1/2008 |
| WO | WO 2008/044615 | 4/2008 |
| WO | WO 2008/142685 | 11/2008 |
| WO | WO 2009/027394 | 3/2009 |
| WO | WO 2009/122395 | 10/2009 |
| WO | WO 2010/091440 | 8/2010 |
| WO | WO 2011/004820 | 1/2011 |
| WO | WO 2014/190026 | 11/2014 |
| WO | WO 2015/064616 | 5/2015 |
| WO | WO 2015/123313 | 8/2015 |
| WO | WO 2016/186876 | 11/2016 |
| WO | WO 2016/193820 | 12/2016 |
| WO | WO 2017/066063 | 4/2017 |

* cited by examiner

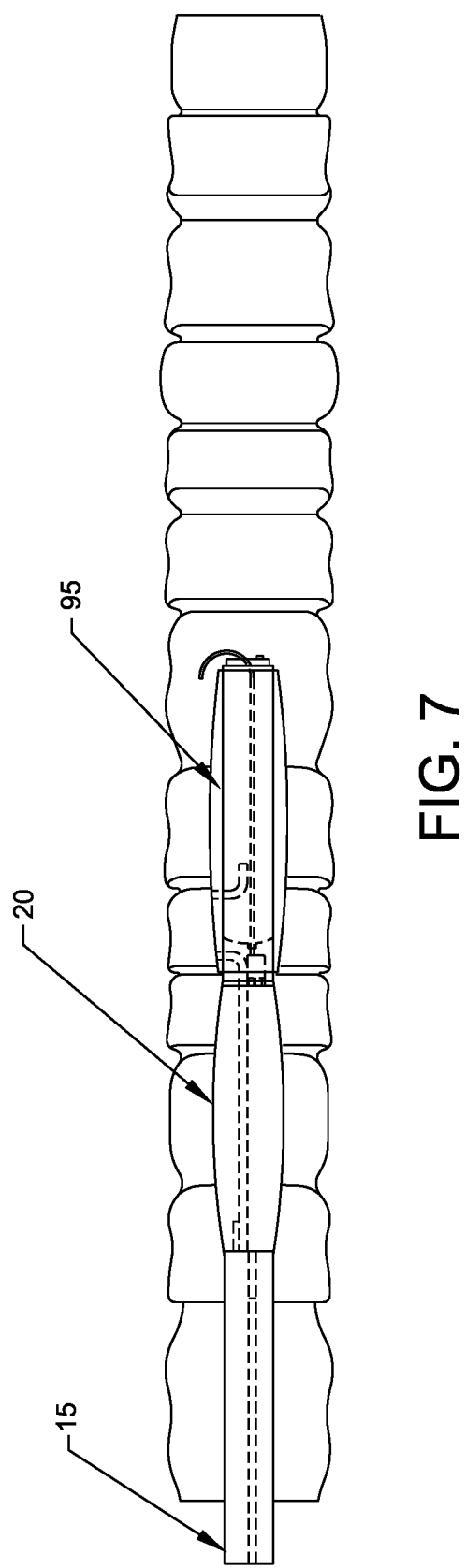

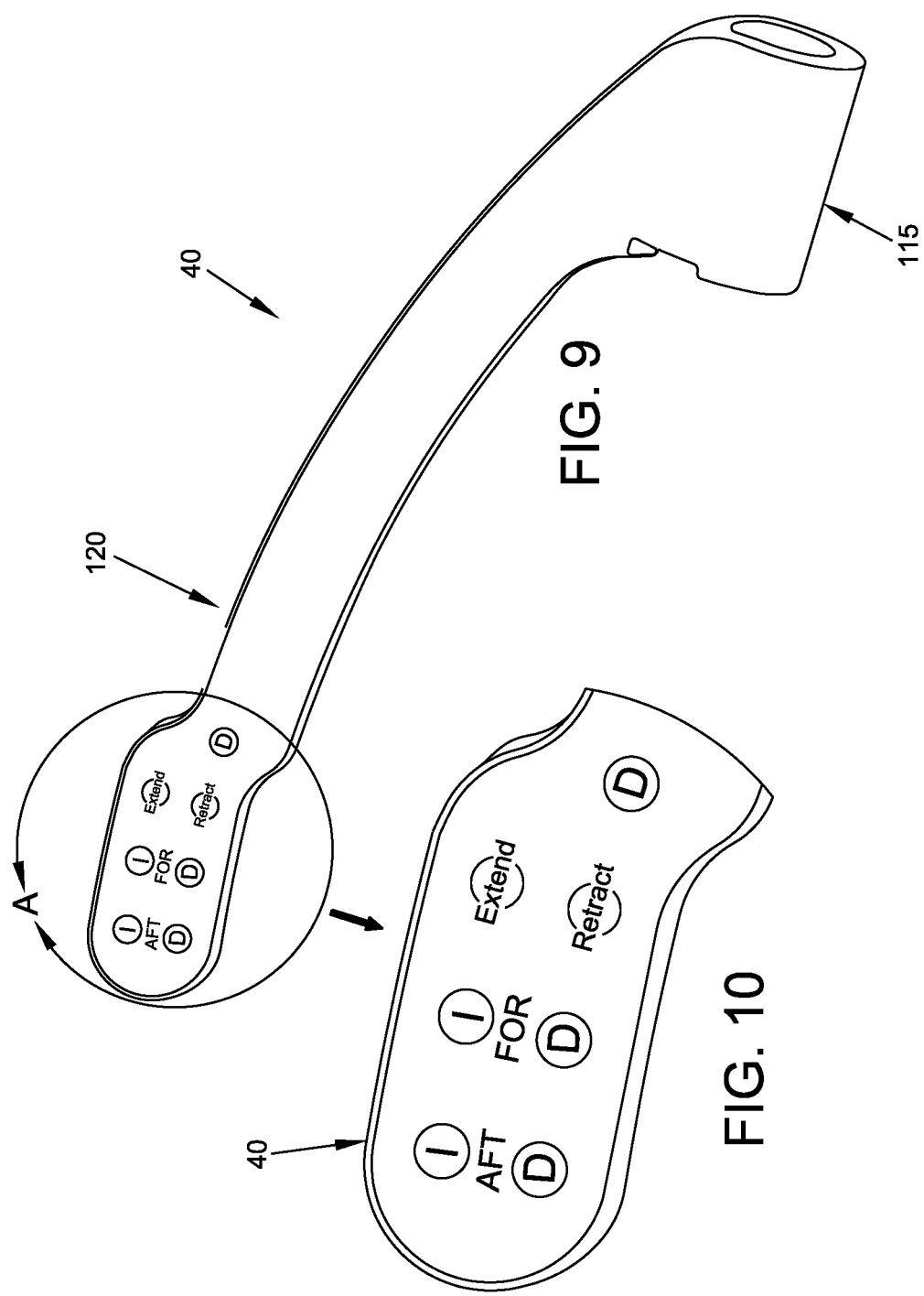

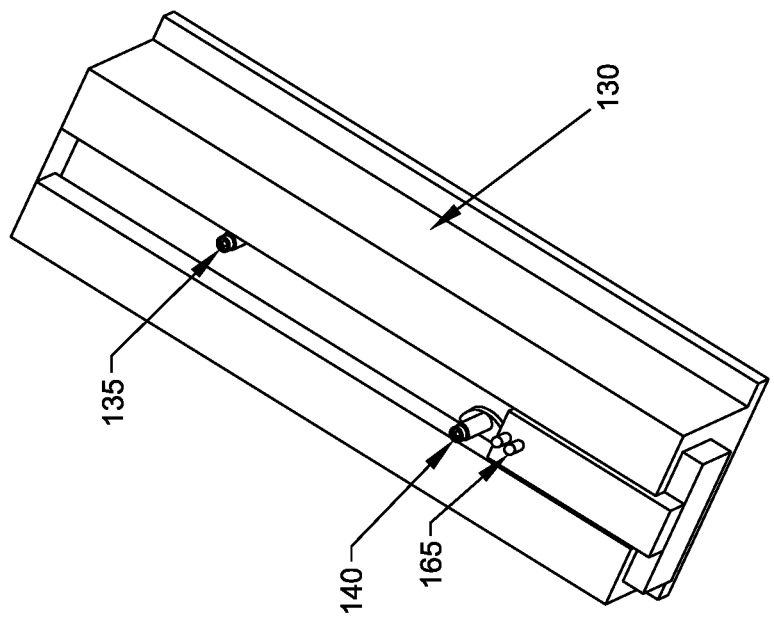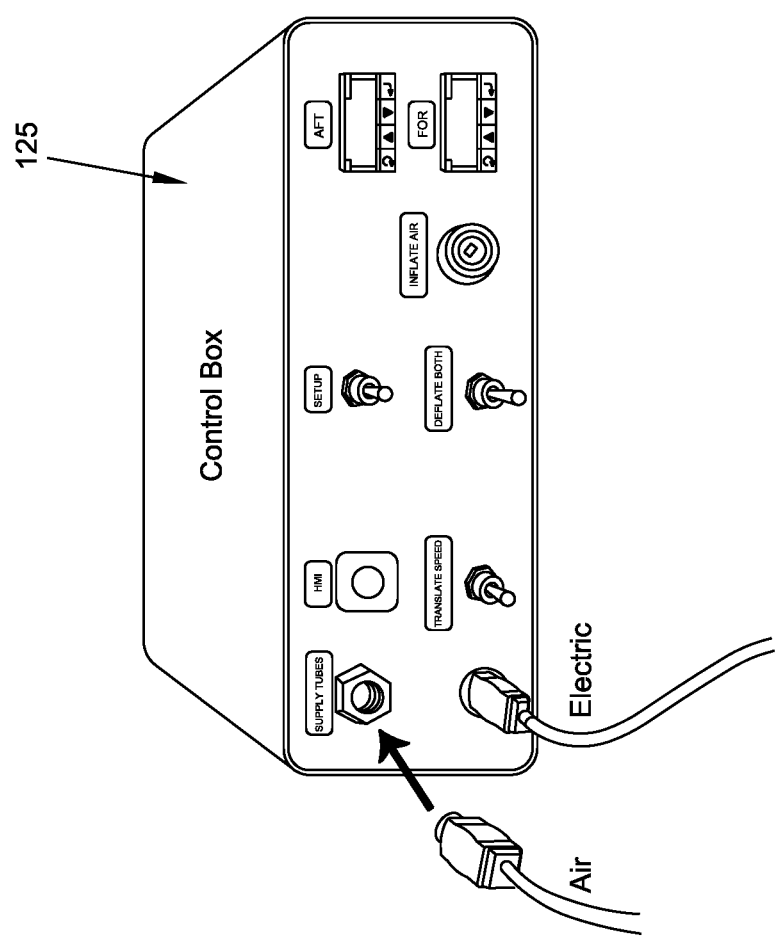
FIG. 13

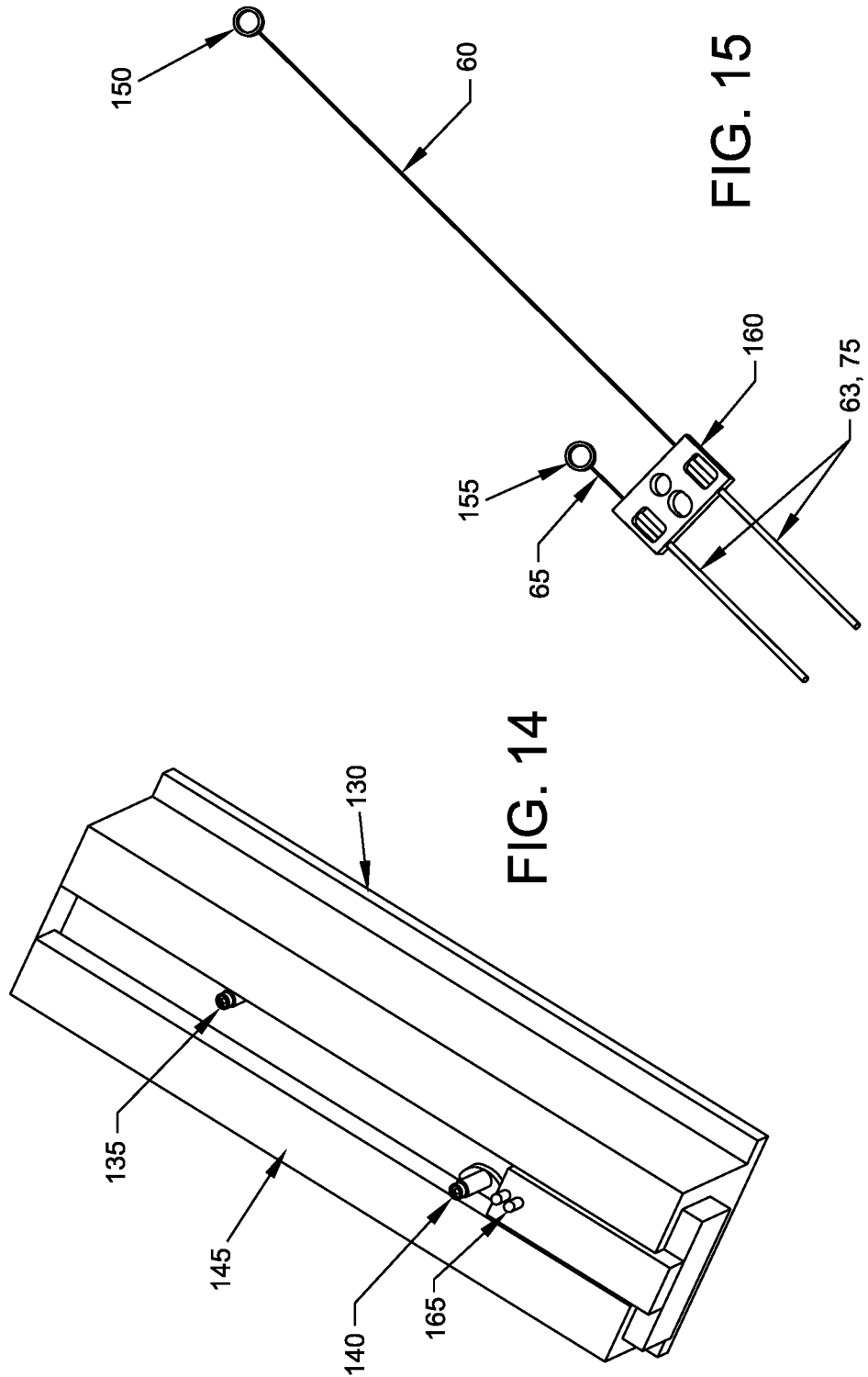

2. PULL DISPOSABLE DEVICE OVER SCOPE THEN REMOVE CONDOM FROM TIP OF SCOPE

4. INJECT 10-20cc OF SALINE INTO SYSTEM, ADVANCE GUIDE WIRE TO TIP OF SCOPE

5. INSERT SCOPE INTO PATIENT

6. ADVANCE TO DESIRE LOCATION
(TOP VIEW)

7. STOP AT DESIRE LOCATION IN COLON

10. EXTEND FORE BALLOON OVER GUIDE WIRE

11. INFLATE FORE BALLOON TO UNFOLD LUMEN BEND

13. USE OF SURGICAL TOOLS WITH GOOD CONTROL OF SURGICAL FIELD

14. ISOLATED THERAPEUTIC ZONE ENABLES RAPID FLUSHING

15. SEALED ZONE IS FILLED WITH FLUID VIA WORKING CHANNEL

16. SUCTIONING OUT FLUID FOR FURTHER EVALUATION OF BLEEDING

18. WITHDRAWAL WITH USE OF FORE BALLOON INFLATION

19. INFLATED FORE BALLOON USED AS BRAKE

21. SCOPE WITHDRAWAL PASSING THROUGH SECTION DEF

METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

REFERENCE TO PENDING PRIOR PATENT APPLICATION

This patent application is a continuation of pending prior U.S. patent application Ser. No. 14/540,355, filed Nov. 13, 2014 by Cornell University for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which in turn is a continuation of prior U.S. patent application Ser. No. 12/969,059, filed Dec. 15, 2010 by Jeffrey Milsom et al. for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which claims benefit of prior U.S. Provisional Patent Application Ser. No. 61/284,215, filed Dec. 15, 2009 by Jeffrey Milsom et al. for METHOD AND APPARATUS FOR STABILIZING, STRAIGHTENING, EXPANDING AND/OR FLATTENING THE SIDE WALL OF A BODY LUMEN OR BODY CAVITY SO AS TO PROVIDE INCREASED VISUALIZATION OF THE SIDE WALL OF THE BODY LUMEN OR BODY CAVITY, AND/OR FOR STABILIZING INSTRUMENTS RELATIVE TO THE SAME.

The three (3) above-identified patent applications are hereby incorporated herein by reference.

FIELD OF THE INVENTION

This invention relates to surgical methods and apparatus in general, and more particularly to surgical methods and apparatus for stabilizing, straightening, expanding and/or flattening the side wall of a body lumen and/or body cavity so as to provide increased visualization of the same and/or increased access to the same, and/or for stabilizing instruments relative to the same.

BACKGROUND OF THE INVENTION

The human body comprises many different body lumens and body cavities. By way of example but not limitation, the human body comprises body lumens such as the gastrointestinal (GI) tract, blood vessels, lymphatic vessels, the urinary tract, etc. By way of further example but not limitation, the human body comprises body cavities such as the head, chest, abdomen, nasal sinuses, cavities within organs, etc.

In many cases it may be desirable to endoscopically examine and/or treat a disease process or abnormality located within, or on the side wall of, a body lumen and/or body cavity. By way of example but not limitation, it may be desirable to examine the side wall of the gastrointestinal tract for lesions and, if a lesion is found, to biopsy, remove and/or otherwise treat the lesion.

The endoscopic examination and/or treatment of the side wall of a body lumen and/or body cavity can be complicated by the geometry of the side wall of the body lumen and/or body cavity, and/or by the consistency of the tissue making up the side wall of the body lumen and/or body cavity. By way of example but not limitation, the intestine is an elongated organ having an inner lumen characterized by frequent turns and a side wall characterized by numerous folds, with the side wall tissue having a relatively soft, pliable consistency. It can be difficult to fully visualize the side wall of the intestine, and/or to treat a lesion formed on the side wall of the intestine, due to this varying side wall geometry and its soft, pliable consistency. By way of example but not limitation, in the case of colonoscopies, it has been found that approximately 5-30% of patients have a tissue geometry and/or a tissue consistency which makes it difficult to fully visualize the anatomy using conventional endoscopes, and/or to fully access the anatomy using instruments introduced through conventional endoscopes.

In addition to the foregoing, it has also been found that some body lumens and/or body cavities can spasm and/or contract when an endoscope is inserted into the body lumen and/or body cavity. This spasming and/or contraction can cause the body lumen and/or body cavity to constrict and/or otherwise move and/or change its configuration, which can further complicate and/or compromise endoscopic visualization of the anatomy, and/or further complicate and/or compromise access to the anatomy using instruments introduced through conventional endoscopes.

Since the ability of medical personnel to directly examine inner surfaces of the body is constantly increasing with the improvement and expansion of new endoscopic devices, it would, therefore, be highly advantageous to provide an endoscopic device capable of stabilizing, straightening, expanding and/or flattening the side wall of a body lumen and/or body cavity so as to better present the side wall tissue for examination and/or treatment during an endoscopic procedure.

It would also be highly advantageous to provide an endoscopic device capable of steadying and/or stabilizing the distal tips and/or working ends of instruments inserted into a body lumen and/or body cavity, whereby to facilitate the use of those instruments.

SUMMARY OF THE INVENTION

The present invention comprises the provision and use of a novel endoscopic device which is capable of stabilizing, straightening, expanding and/or flattening the side wall of a body lumen and/or body cavity so as to better present the side wall tissue for examination and/or treatment during an endoscopic procedure.

The present invention also comprises the provision and use of a novel endoscopic device capable of steadying and/or stabilizing the distal tips and/or working ends of instruments inserted into a body lumen and/or body cavity, whereby to facilitate the use of those instruments.

In one form of the present invention, there is provided apparatus comprising:

a sleeve adapted to be slid over the exterior of an endoscope;

a proximal balloon secured to the sleeve near the distal end of the sleeve;

a pusher tube slidably mounted to the sleeve, the pusher tube being configured to slidably receive a guidewire therein; and a distal balloon secured to the distal end of the pusher tube.

In another form of the present invention, there is provided apparatus comprising:

a sleeve adapted to be slid over the exterior of an endoscope;

a proximal balloon secured to the sleeve near the distal end of the sleeve;

a pusher element slidably mounted to the sleeve;

a double pull mechanism mounted to the sleeve for moving the pusher element relative to the sleeve; and a distal balloon secured to the distal end of the pusher element.

In another form of the present invention, there is provided apparatus comprising:

a sleeve adapted to be slid over the exterior of an endoscope;

a proximal balloon secured to the sleeve near the distal end of the sleeve;

a pusher element slidably mounted to the sleeve, the pusher element being substantially flexible, having substantial column strength, and having a length substantially shorter than the sleeve; and a distal balloon secured to the distal end of the pusher element.

In another form of the present invention, there is provided a method for performing a procedure in a body lumen and/or body cavity, the method comprising:

providing apparatus comprising:
 a sleeve adapted to be slid over the exterior of an endoscope;
 a proximal balloon secured to the sleeve near the distal end of the sleeve;
 a pusher tube slidably mounted to the sleeve, the pusher tube being configured to slidably receive a guidewire therein; and
 a distal balloon secured to the distal end of the pusher tube;

positioning the apparatus in the body lumen and/or body cavity;

inflating the proximal balloon;

advancing a guidewire through the pusher tube;

advancing the pusher tube along the guidewire;

inflating the distal balloon; and performing the procedure.

In another form of the present invention, there is provided a method for performing a procedure in a body lumen and/or body cavity, the method comprising:

providing apparatus comprising:
 a sleeve adapted to be slid over the exterior of an endoscope;
 a proximal balloon secured to the sleeve near the distal end of the sleeve;
 a pusher element slidably mounted to the sleeve;
 a double pull mechanism mounted to the sleeve for moving the pusher element relative to the sleeve; and
 a distal balloon secured to the distal end of the pusher tube;

positioning the apparatus in the body lumen and/or body cavity;

inflating the proximal balloon;

advancing the pusher element distally relative to the sleeve;

inflating the distal balloon; and performing the procedure.

In another form of the present invention, there is provided a method for performing a procedure in a body lumen and/or body cavity, the method comprising:

providing apparatus comprising:
 a sleeve adapted to be slid over the exterior of an endoscope;
 a proximal balloon secured to the sleeve near the distal end of the sleeve;
 a pusher element slidably mounted to the sleeve, the pusher element being substantially flexible, having substantial column strength, and having a length substantially shorter than the sleeve; and
 a distal balloon secured to the distal end of the pusher element;

positioning the apparatus in the body lumen and/or body cavity;

inflating the proximal balloon;

advancing the pusher element distally relative to the sleeve;

inflating the distal balloon; and performing the procedure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 2-6, 6A and 7-12 are schematic views showing further details of the endoscopic stabilizing platform shown in FIG. 1;

FIGS. 13-15 are schematic views showing a controller for operating the endoscopic stabilizing platform of the present invention, and further aspects of the present invention, including a motorized drive system for use in conjunction with the endoscopic stabilizing platform of the present invention;

DETAILED DESCRIPTION OF THE PREFERRED EMBODIMENTS

The Novel Endoscopic Stabilizing Platform

The present invention comprises the provision and use of a novel endoscopic stabilizing platform for stabilizing, straightening, expanding and/or flattening the side wall of a body lumen and/or body cavity so as to better present the side wall tissue for examination and/or treatment during an endoscopic procedure, and/or for stabilizing instruments relative to the same. By way of example but not limitation, the novel endoscopic stabilizing platform can be used to stabilize, straighten, expand and/or flatten bends and/or curves and/or folds in the side wall of a body lumen and/or body cavity so as to better present the side wall tissue for examination and/or treatment during an endoscopic procedure, and can provide a stable platform for the performance of numerous procedures within the body lumen and/or body cavity, including the stabilization of an endoscope and/or other surgical instruments within the body lumen and/or body cavity, e.g., during a lesion biopsy and/or lesion removal procedure, an organ resection procedure, etc.

As used herein, the term "endoscopic procedure" is intended to mean substantially any minimally-invasive or limited access procedure, diagnostic and/or surgical, for accessing the interior of a body lumen and/or body cavity for the purposes of viewing, biopsying and/or treating tissue, including removing a lesion and/or resecting tissue, etc.

Figure 1:
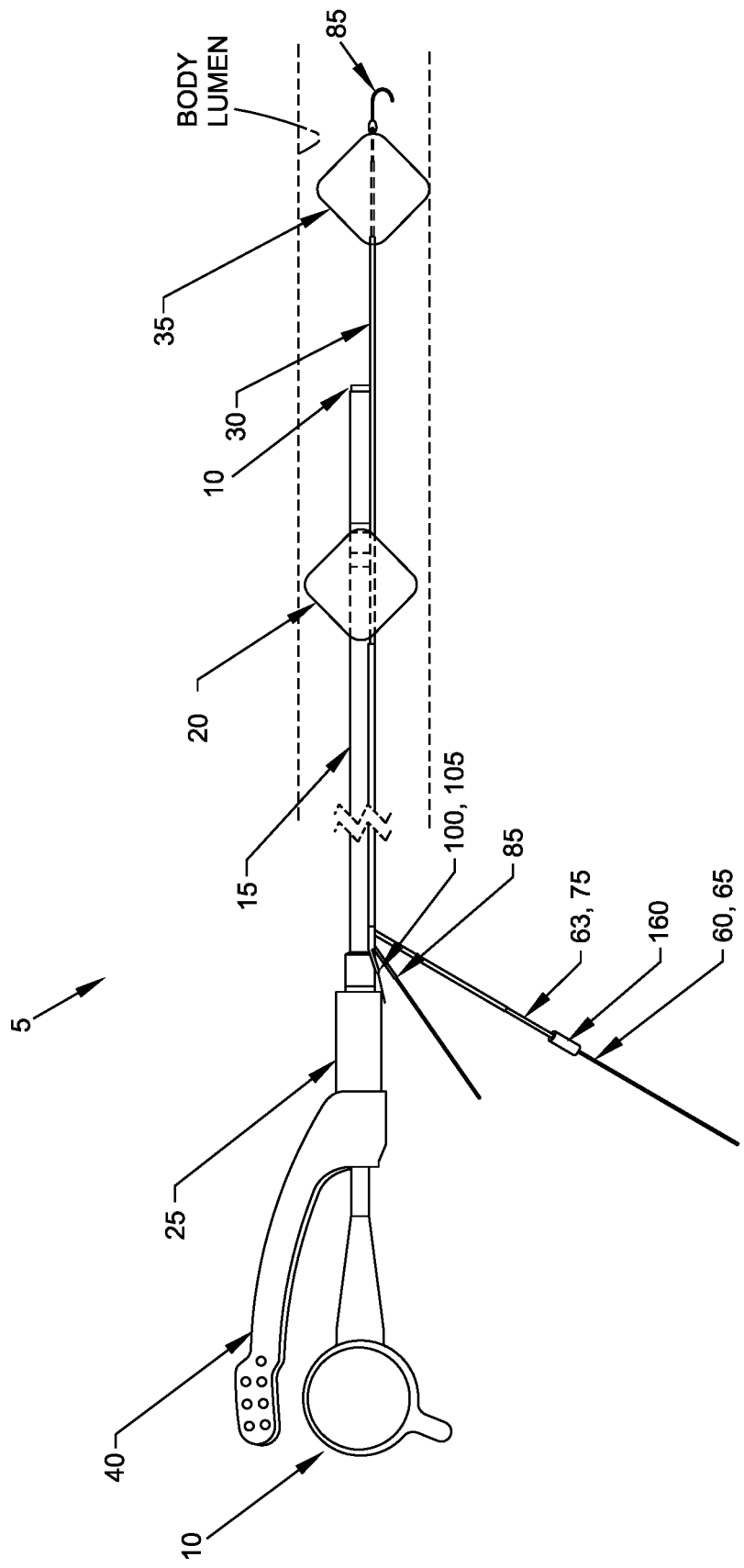
FIG. 1 is a schematic side view showing a novel endoscopic stabilizing platform formed in accordance with the present invention, wherein the endoscopic stabilizing platform is shown mounted on an endoscope and deployed in a body lumen so as to stabilize, straighten, expand and/or flatten the side wall of the body lumen in order to provide increased visualization of the same and/or to provide increased stability for the distal tips and/or working ends of instruments inserted into the body lumen.
Figure 2:
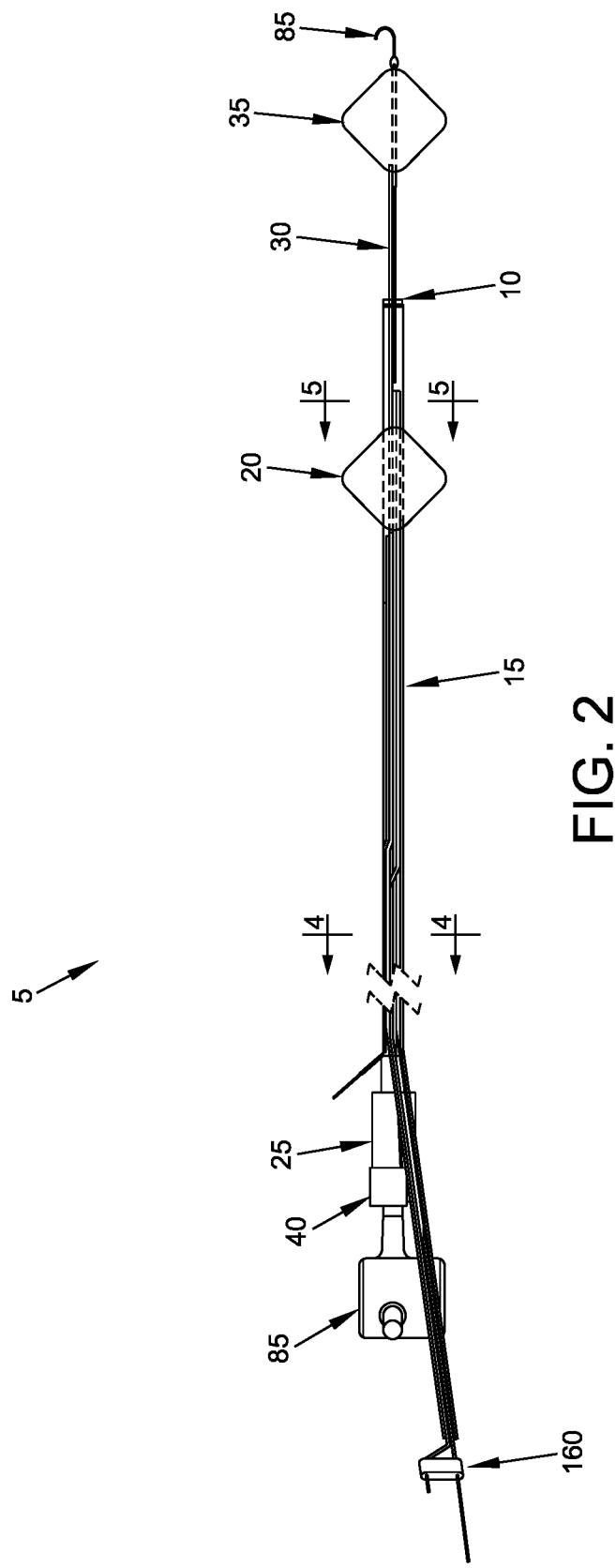
Figure 3:
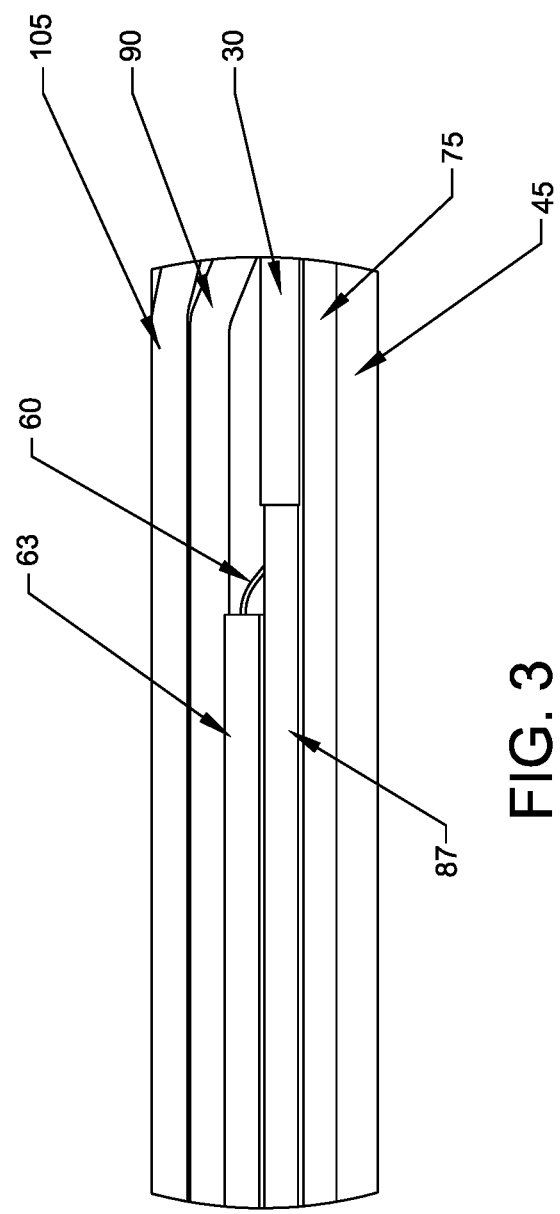
Figure 4:
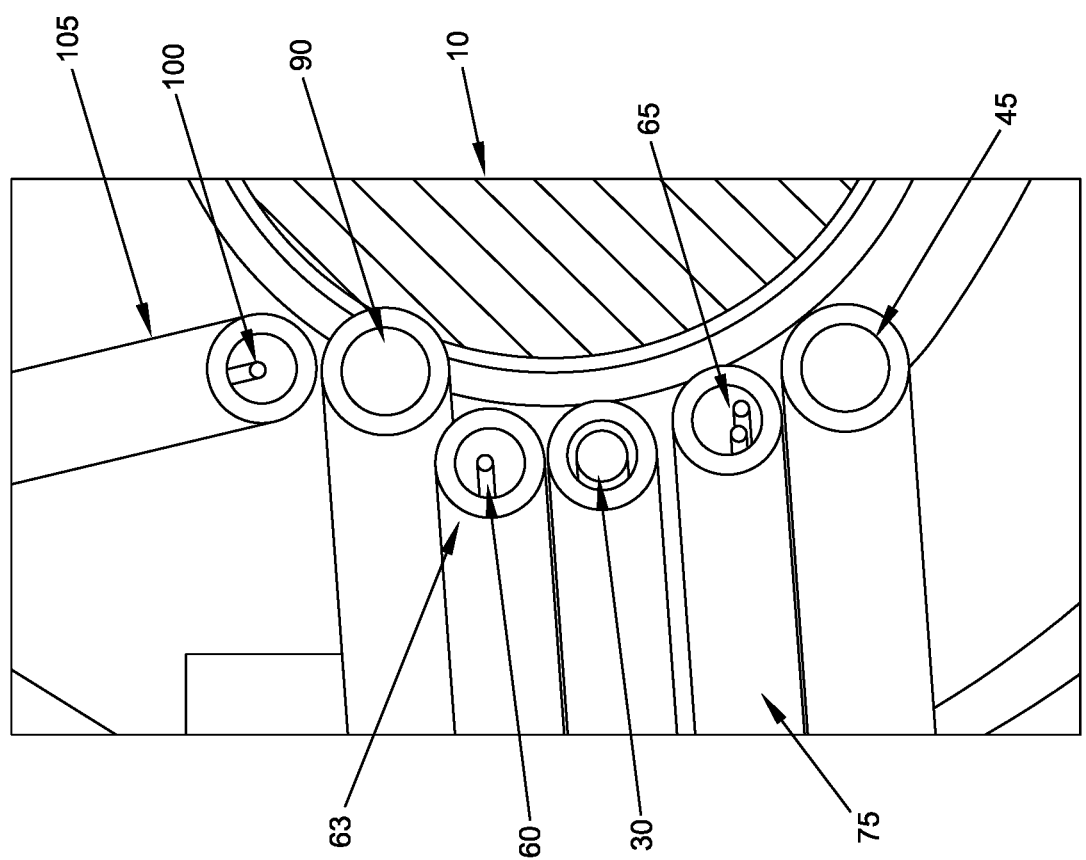
Figure 5:
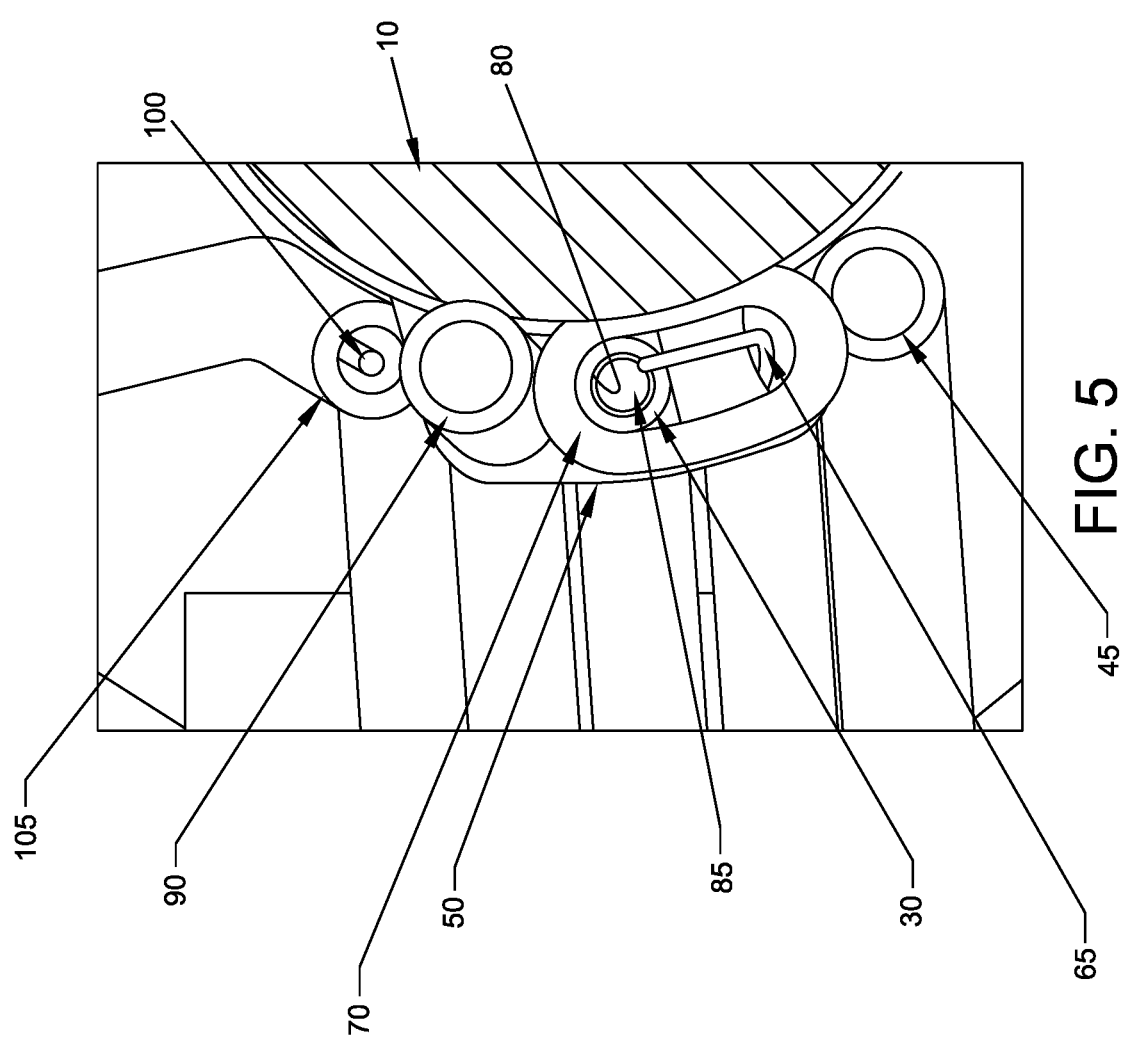

In accordance with the present invention, and looking now at FIG. 1, there is shown an endoscopic stabilizing platform 5 capable of stabilizing, straightening, expanding and/or flattening the side wall of a body lumen and/or body cavity so as to better present the side wall tissue for examination and/or treatment during an endoscopic procedure using an endoscope 10, and/or for stabilizing the distal tips and/or working ends of instruments (not shown in FIG. 1) relative to the same.

More particularly, endoscopic stabilizing platform 5 generally comprises a sleeve 15 adapted to be slid over the exterior of the shaft of endoscope 10 as will hereinafter be discussed, a proximal (or "aft") balloon 20 secured to sleeve 15 near the distal end of the sleeve, and a handle 25 secured to sleeve 15 at the proximal end of the sleeve. Endoscopic stabilizing platform 5 also comprises a pusher tube 30 slidably mounted to sleeve 15 as will hereinafter be discussed, and a distal (or "fore") balloon 35 secured to the distal end of pusher tube 30, whereby the spacing between proximal balloon 20 and distal balloon 35 can be adjusted by the surgeon during use by moving pusher tube 30 relative to sleeve 15. Endoscopic stabilizing platform 5 also comprises a hand piece 40 for enabling operation of endoscopic stabilizing platform 5 by a surgeon.

Looking next at FIGS. 1-6 and 6A, sleeve 15 generally comprises an elongated, thin-walled tube configured to be slid over the exterior of the shaft of endoscope 10 so as to make a close fit therewith, such that the sleeve will slide easily over the endoscope during mounting but will have sufficient residual friction with the outer surface of the endoscope that the sleeve will remain in place during use. Sleeve 15 is sized so that when its distal end is substantially aligned with the distal end of endoscope 10, sleeve 15 (and handle 25) will substantially cover the shaft of the endoscope. Sleeve 15 preferably has a smooth outer surface so as to be non-traumatic to tissue, and is preferably made of a highly flexible material such that the sleeve will not inhibit bending of the endoscope during use. In one preferred form of the invention, sleeve 15 comprises polyethylene. If desired, sleeve 15 can include a lubricious coating on some or all of its interior and/or exterior surfaces, so as to facilitate disposition of the sleeve over the endoscope and/or movement of endoscopic stabilizing platform 5 through a body lumen and/or body cavity, respectively.

Proximal (or "aft") balloon 20 is secured to sleeve 15 near the distal end of the sleeve. Proximal balloon 20 is disposed concentrically about sleeve 15, and hence concentrically about endoscope 10 disposed within sleeve 15. Proximal balloon 20 may be selectively inflated/deflated by means of a proximal inflation/deflation tube 45 which is secured to the exterior surface of sleeve 15, whereby proximal balloon 20 may be selectively secured to/released from the adjacent anatomy, respectively, as will hereinafter be discussed. Preferably proximal balloon 20 is disposed a short distance back from the distal end of sleeve 15, i.e., by a distance which is approximately the same as the length of the flexible portion of an endoscope, so that the flexible portion of an endoscope will be disposed distal to the proximal balloon 20 when the endoscope is disposed in sleeve 15. This construction allows the flexible portion of the endoscope to be articulated even when proximal balloon 20 has been inflated in the anatomy so as to stabilize the adjacent non-articulating portion of the endoscope relative to the anatomy, as will hereinafter be discussed in further detail.

Handle 25 is secured to the proximal end of sleeve 15. Handle 25 preferably comprises a substantially rigid or semi-rigid structure which may be gripped by the hand of the surgeon and pulled proximally so as to pull sleeve 15 over the exterior surface of endoscope 10, whereby to mount sleeve 15 to the shaft of the endoscope.

Pusher tube 30 is slidably mounted to sleeve 15, whereby the distal end of the pusher tube can be extended and/or retracted relative to sleeve 15, and hence extended and/or retracted relative to the distal end of endoscope 10 disposed in sleeve 15.

Figure 6:
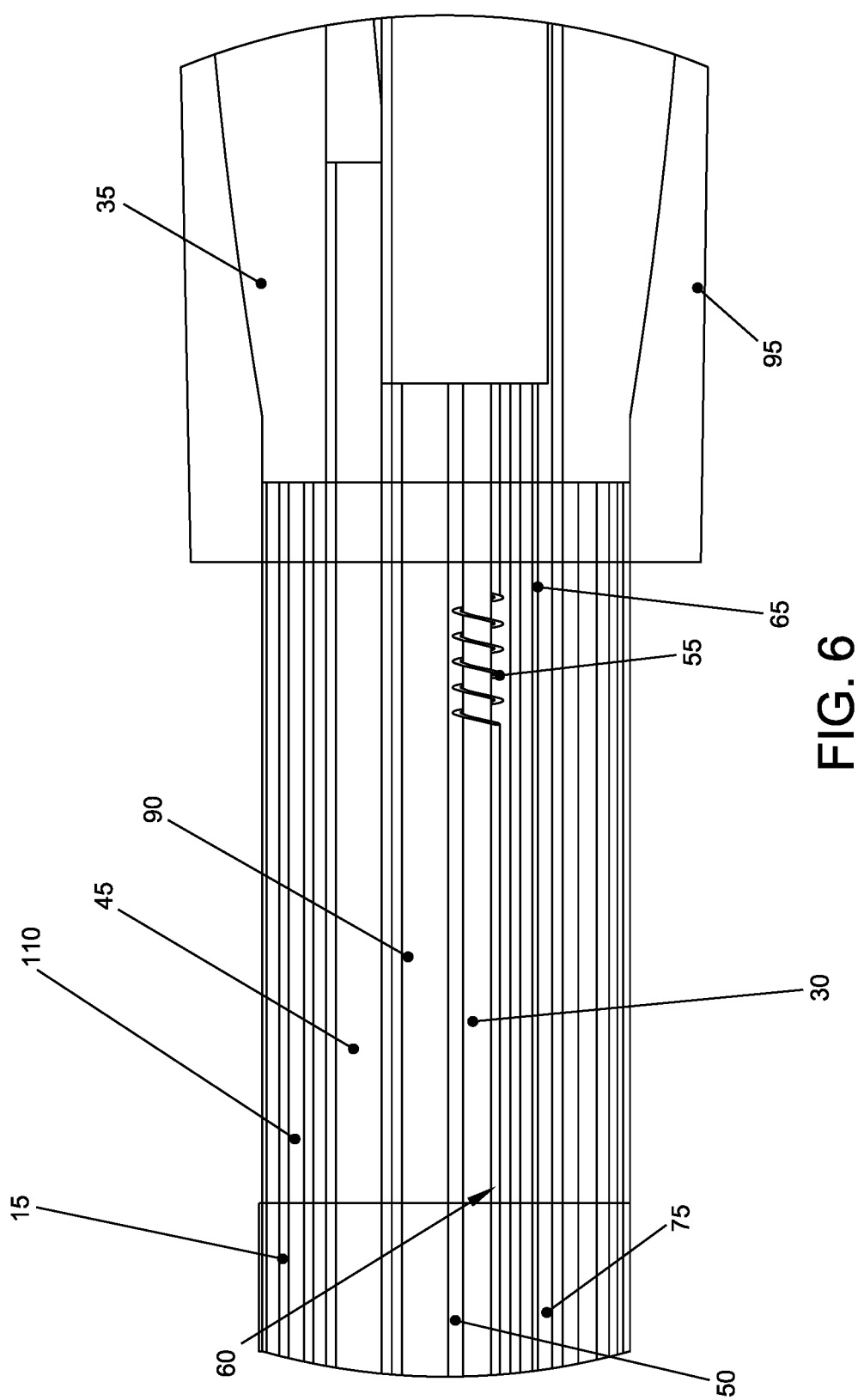
Figure 6A:
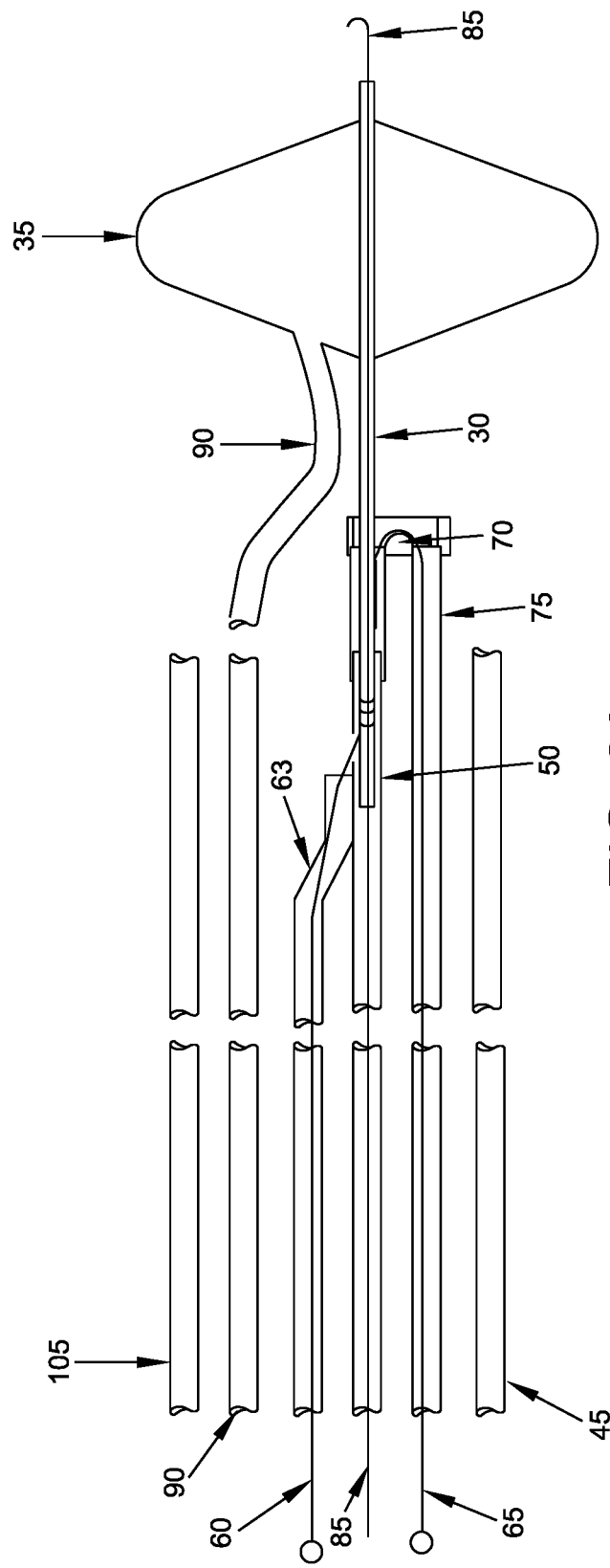

More particularly, pusher tube 30 is a relatively short element which is slidably disposed in a support tube 50 which is secured to the outer surface of sheath 15. Pusher tube 30 is preferably formed out of a relatively flexible material which provides good column strength, e.g., a superelastic material such as a shape memory alloy. By way of example but not limitation, pusher tube 30 may be formed out of Nitinol. A double pull line 55 is secured to the outer surface of pusher tube 30, e.g., by wrapping the double pull line around the outer surface of the proximal end of pusher tube 30 and gluing it in place (FIG. 6). Double pull line 55 has a retract line 60 which extends proximally through support tube 50 and then crosses over to a retract tube 63. The proximal end of retract line 60 exits retract tube 63 adjacent the proximal end of sleeve 15, e.g., near handle 25. Double pull line 55 also has an extend line 65 which extends distally through support tube 50, around a "pulley" (i.e., bearing structure) 70 (FIG. 5) disposed at the distal end of support tube 50, and then back through an extend tube 75 which is secured to the outer surface of sleeve 15. The proximal end of extend line 65 exits extend tube 75 adjacent the proximal end of sleeve 15, e.g., near handle 15. As a result of this construction, pulling the proximal end of retract line 60 proximally causes the distal end of pusher tube 30 to retract proximally relative to sleeve 15, and pulling the proximal end of extend line 65 proximally causes the distal end of pusher tube 30 to extend distally relative to sleeve 15.

Thus it will be seen that a pulling motion, selectively applied to retract line 60 or extend line 65, is used for both retracting and extending pusher tube 30 relative to sleeve 15 (and hence relative to an endoscope 10 disposed in sleeve 15). Furthermore, this pulling motion is applied to the relatively short pusher tube 30 fairly close to the distal end of sleeve 15, and the pusher tube is constructed so as to have a relatively high column strength along its length. As a result, this construction permits a substantial extension force to be applied to the distal end of pusher tube 30, which can be important when traversing a tortuous body lumen deep within the anatomy of a patient, as will hereinafter be discussed. At the same time, since retract line 60 and extend line 65 act in tension, they can be highly flexible, and since pusher tube 30 is relatively short and does not need to extend for the entire length of sleeve 15, pusher tube 30 can be relatively flexible even as it delivers good column strength. As a result, endoscopic stabilizing platform 5 is highly flexible along its length, even as it permits a substantial extension force to be applied to the distal end of pusher tube 30. This is a substantial advance in the art since, in the absence of such a construction, a long pusher tube, having substantial column strength along its entire length, would have to be used to transfer a substantial extension force from the proximal end of the endoscopic stabilizing platform to the distal end of the endoscopic stabilizing platform. But such a long pusher tube, with substantial column strength along its entire length, would undermine the desired flexibility of the endoscopic stabilizing platform.

Thus, as a result of its unique construction, endoscopic stabilizing platform 5 can extend a substantial length into the body, be highly flexible so as to traverse a highly tortuous body lumen (e.g., the GI tract), and still generate a substantial distally-directed force to pusher tube 30.

Pusher tube 30 includes an internal lumen 80 which is sized to accommodate a guidewire 85 therein, which permits pusher tube 30, and hence distal balloon 35 secured to the distal end of pusher tube 30, to be directed by a guidewire 85, as will hereinafter be discussed in further detail. The proximal end of guidewire 85 extends through guidewire tube 87, which is secured to the outer surface of sleeve 15. The proximal end of guidewire 85 exits guidewire tube 87 adjacent the proximal end of sleeve 15, e.g., near handle 25.

Distal (or "fore") balloon 35 is secured to the distal end of pusher tube 30, whereby the spacing between proximal (or "aft") balloon 20 and distal (or "fore") balloon 35 can be adjusted by moving pusher tube 30 relative to sleeve 15. Distal balloon 35 is disposed concentrically about pusher tube 30, and hence concentrically about guidewire 85 disposed within pusher tube 30. Distal balloon 35 may be selectively inflated/deflated by means of a distal inflation/deflation tube 90 which is secured to the exterior surface of sleeve 15, whereby distal balloon 35 may be selectively secured to/released from the adjacent anatomy, respectively. However, the distal end of inflation/deflation tube 90 is not secured to the exterior surface of sleeve 15, and is preferably relatively flexible, so that inflation/deflation tube 90 can accommodate movement of pusher tune 30 (and hence distal balloon 35) relative to sleeve 15.

Figure 8:
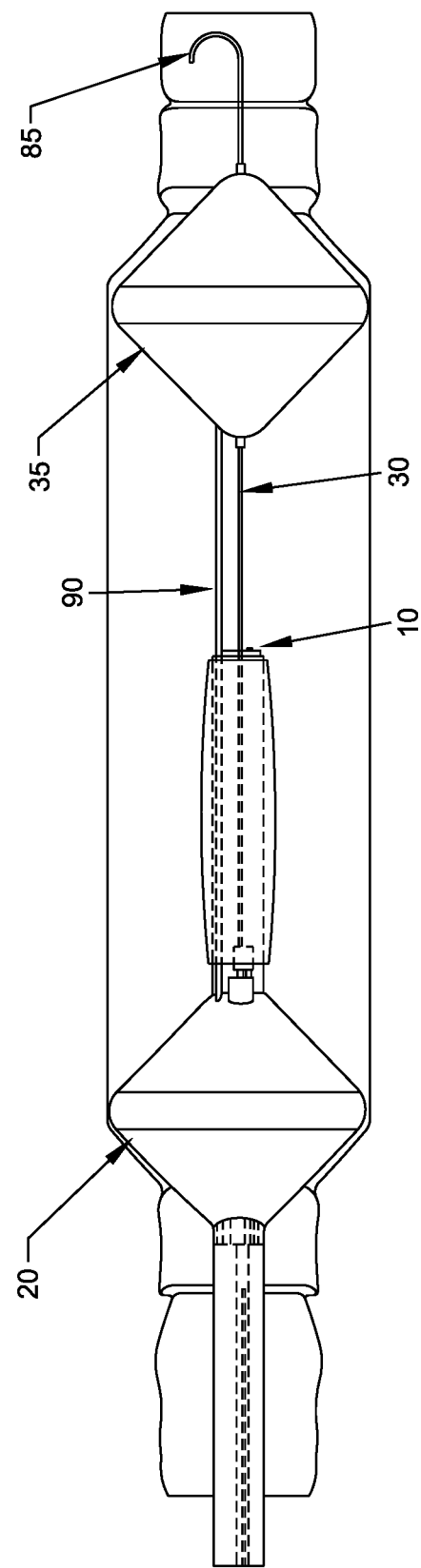
Figure 11:
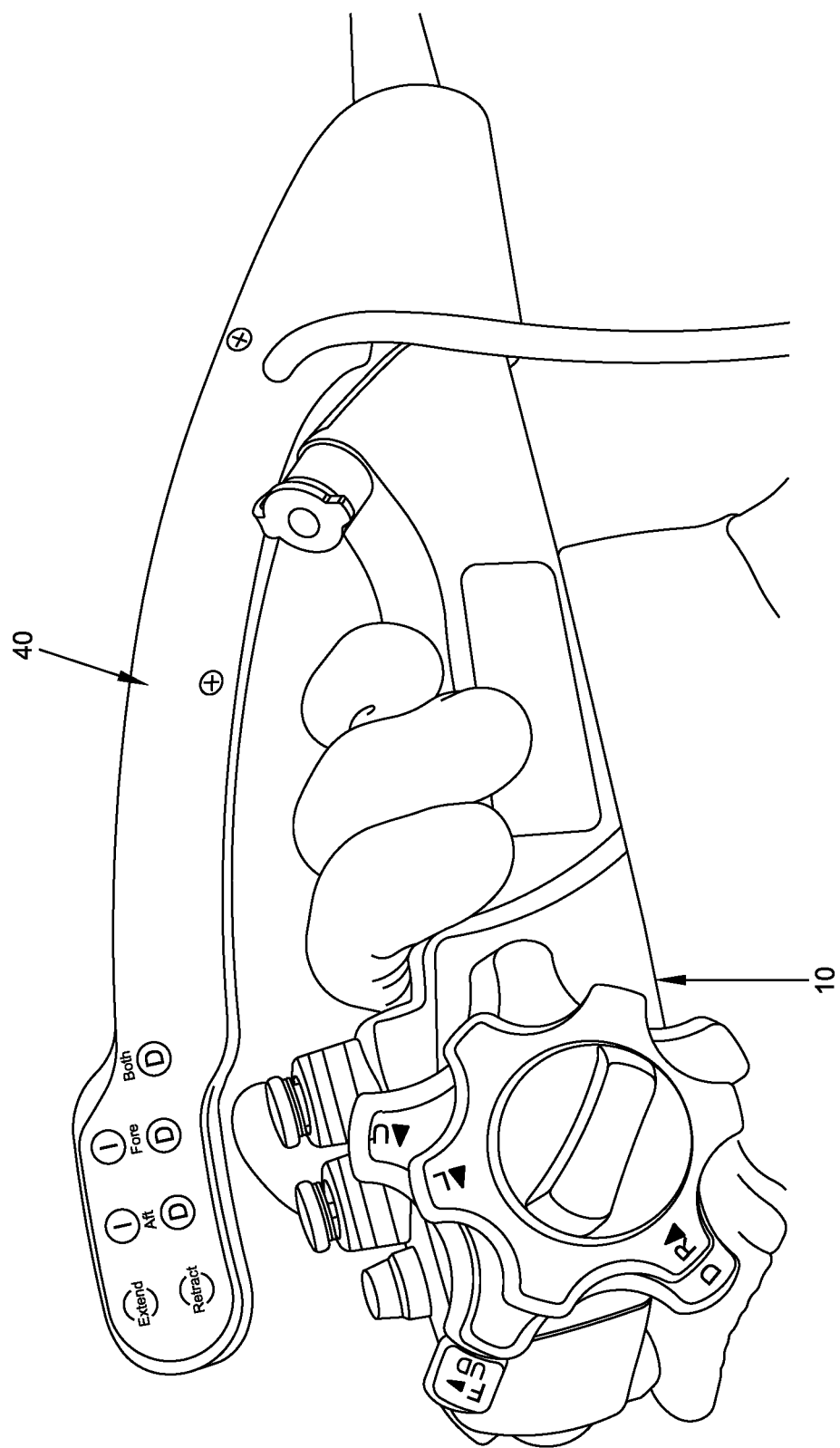
Figure 12:
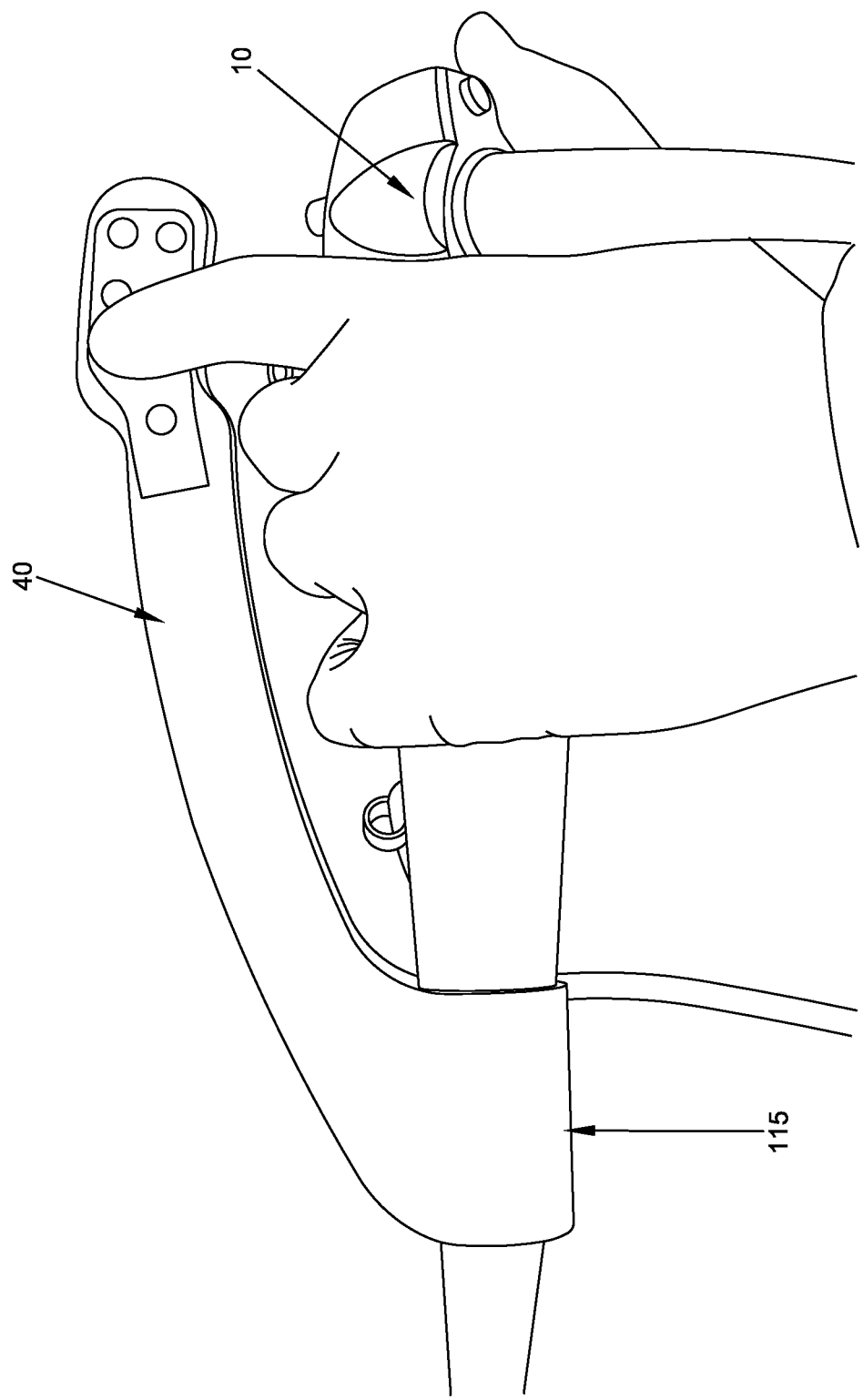
Figure 16:
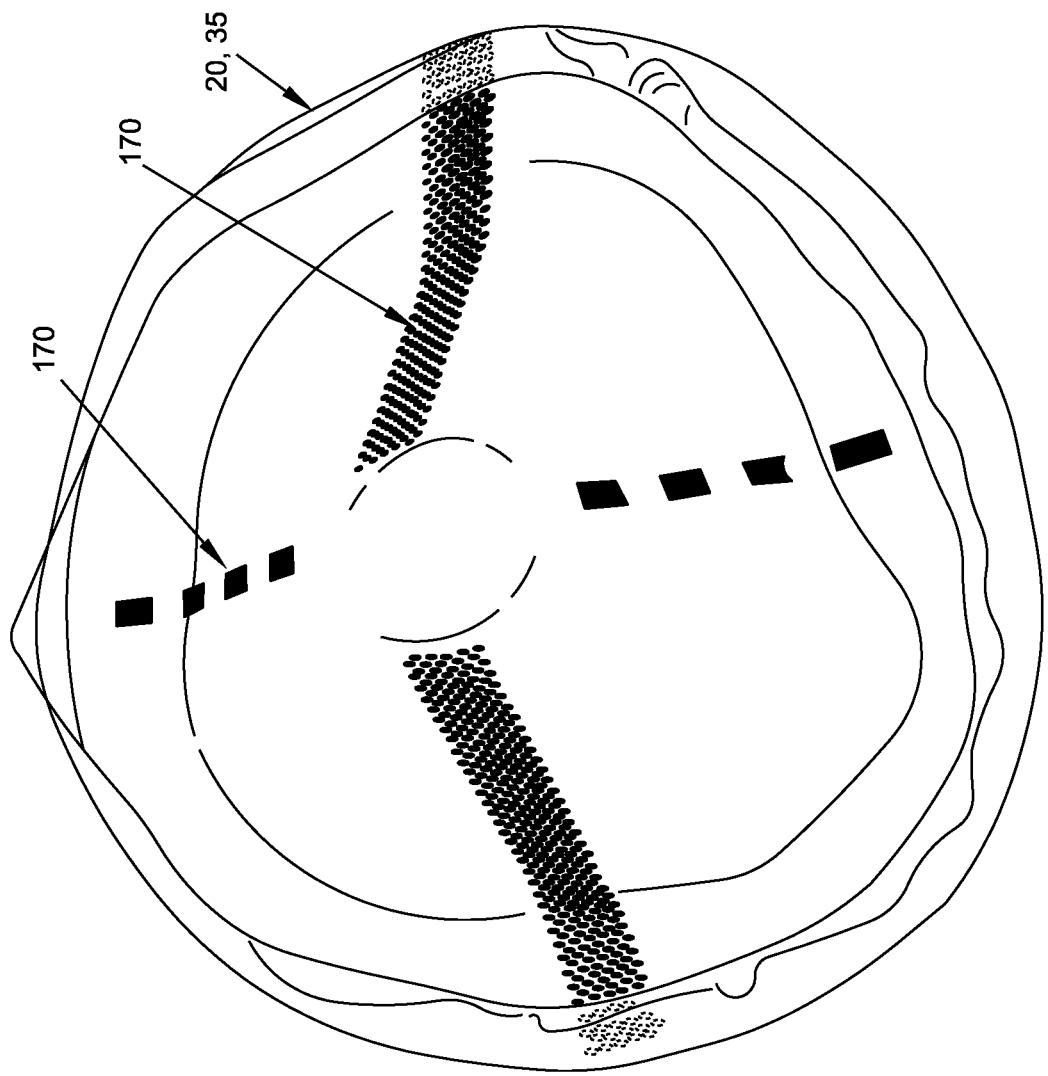
FIG. 16 is a schematic view showing how radiopaque markers may be incorporated into and/or onto one or both of the balloons of the endoscopic stabilizing platform of the present invention.

Preferably, and looking now at FIGS. 6 and 7, a rip sleeve 95 is initially disposed over the deflated proximal balloon 20 and distal balloon 35 so as to facilitate "snag-free" insertion of endoscopic stabilizing platform 5 into and through a body lumen and/or body cavity. When the distal end of endoscopic stabilizing platform 5 has been advanced to the location of use, rip sleeve 95 can be removed by pulling on the proximal end of a rip cord 100, which extends along a rip cord tube 105 which is secured to the outer surface of sleeve 15, whereby to free proximal balloon 20 and distal balloon 35 for subsequent inflation, e.g., in the manner shown in FIG. 8. In this respect it will be appreciated that the proximal end of rip cord 100 exits rip cord tube 105 adjacent the proximal end of sleeve 15, e.g., near handle 25.

Preferably, an overlay sleeve 110 is disposed over exterior surfaces of proximal inflation/deflation tube 45, support tube 50, retract tube 63, extend tube 75, guidewire tube 87, inflation/deflation tube 90 and rip cord tube 105. In one form of the invention, overlay sleeve 110 extends about the entire circumference of sleeve 15 for a portion of the distance between proximal balloon 20 and handle 25. Overlay sleeve 110 helps ensure that the outer surface of endoscopic stabilizing platform 5 is smooth and "snag-free" so that the endoscopic stabilizing platform can move easily within a body lumen and/or body cavity, without causing significant trauma to the tissue. If desired, overlay sleeve 110 can include a lubricious coating on some or all of its exterior surface so as to facilitate movement of endoscopic stabilizing platform 5 through a body lumen and/or body cavity.

Hand piece 40 is shown in FIGS. 1, 2 and 9-12. Hand piece 40 enables single-handed operation of endoscopic stabilizing platform 5 by a surgeon who is simultaneously manipulating endoscope 10. More particularly, hand piece 40 comprises a collar 115 which is adapted to mount over endoscope 10. Collar 115 is configured to be slid over the exterior of the shaft of endoscope 10 so as to make a close fit therewith, such that the collar will slide easily over the endoscope during mounting but will have sufficient residual friction with the outer surface of the endoscope that the hand piece will remain in place during use. Hand piece 40 also comprises an arm 120 which provides controls for advancing/retracting pusher tube 30 relative to sleeve 15, inflating/deflating proximal balloon 20, and/or inflating/deflating distal balloon 35, as will hereinafter be discussed in further detail. Note that arm 120 is configured so as to place the aforementioned controls immediately adjacent to the endoscope controls, whereby to permit easy one-hand operation by the surgeon.

Hand piece 40 is preferably configured to operate in conjunction with a controller 125 (FIG. 13), with hand piece 40 providing the means by which the surgeon controls operation of controller 125. Controller 125 is adapted to supply/withdraw fluid (e.g., air, saline, etc.) to/from proximal balloon 20 and/or distal balloon 35, whereby to selectively inflate/deflate one or the other, or both, of the balloons. Controller 125 is also adapted to control operation of a motorized drive system 130 (FIGS. 13 and 14) which is adapted to (i) selectively apply a pulling force to the proximal end of retract line 60, whereby to retract pusher tube 30 relative to sleeve 15, (ii) selectively apply a pulling force to the proximal end of extend line 65, whereby to extend pusher tube 30 relative to sleeve 15, or (iii) not apply a pulling force to either retract line 60 or extend line 65. The ability of motorized drive system 130 to not apply a pulling force to either retract line 60 or extend line 65 is an important aspect of the present invention, since it means that motorized drive system 130 can hold pusher tube 30 (and hence distal balloon 35) in a fixed position relative to sleeve 15 (and hence endoscope 10), which can be extremely important in stabilizing endoscope stabilizing platform 5 relative to the anatomy.

To this end, motorized drive system 130 preferably comprises a retract pull pin 135 and an extend pull pin 140 which are adapted to be selectively moved relative to a base 145. Retract pull pin 135 is adapted to receive an eyelet 150 (FIG. 15) formed at the proximal end of retract line 60, and extend pull pin 140 is adapted to receive an eyelet 155 formed at the proximal end of extend line 65. Preferably, a cassette 160 (FIG. 15) provides support for retract line 60 and extend line 65, with cassette 160 being received on cassette locating pins 165 disposed on motorized drive system 130.

On account of the foregoing arrangements, a surgeon can use the controls on hand piece 40 to cause controller 125 to selectively inflate/deflate proximal balloon 20, and/or inflate/deflate distal balloon 35. Furthermore, a surgeon can use the controls on hand piece 40 to cause controller 125 to selectively (i) retract pusher tube 30 relative to sleeve 15, (ii)

extend pusher tube 30 relative to sleeve 15, or (iii) hold pusher tube 30 stationary relative to sleeve 15.

If desired, one or both of proximal balloon 20 and distal balloon 35 may include radiopaque markers 170 thereon, whereby to facilitate visualization of balloon location under X-ray or fluoroscopic viewing.

Furthermore, if desired, means can be provided (e.g., at controller 125) to monitor the pressure within proximal balloon 20 and distal balloon 35, whereby to prevent balloon rupture and/or the application of excessive balloon pressure against the adjacent anatomy, both of which could cause trauma to the anatomy. Such means will be obvious to a person of ordinary skill in the art in view of the present disclosure.

And, if desired, means could be provided (e.g., at controller 125 and/or motorized drive system 130) to limit the distal extension force applied to pusher tube 30, again to avoid trauma to the anatomy. Such means will be obvious to a person of ordinary skill in the art in view of the present disclosure.

Significantly, all of endoscopic stabilizing platform 5, with the possible exception of hand piece 40 (and, of course related controller 125 and the related motorized drive system 130) may be disposed of at the conclusion of a procedure.

Preferred Method of Using the Novel Endoscopic Stabilizing Platform

Endoscopic stabilizing platform 5 may be used to stabilize, straighten, expand and/or flatten the side wall of a body lumen and/or body cavity so as to better present the side wall tissue for examination and/or treatment during an endoscopic procedure using endoscope 10, and/or to stabilize the distal tips and/or working ends of instruments relative to the same.

Figure 17:
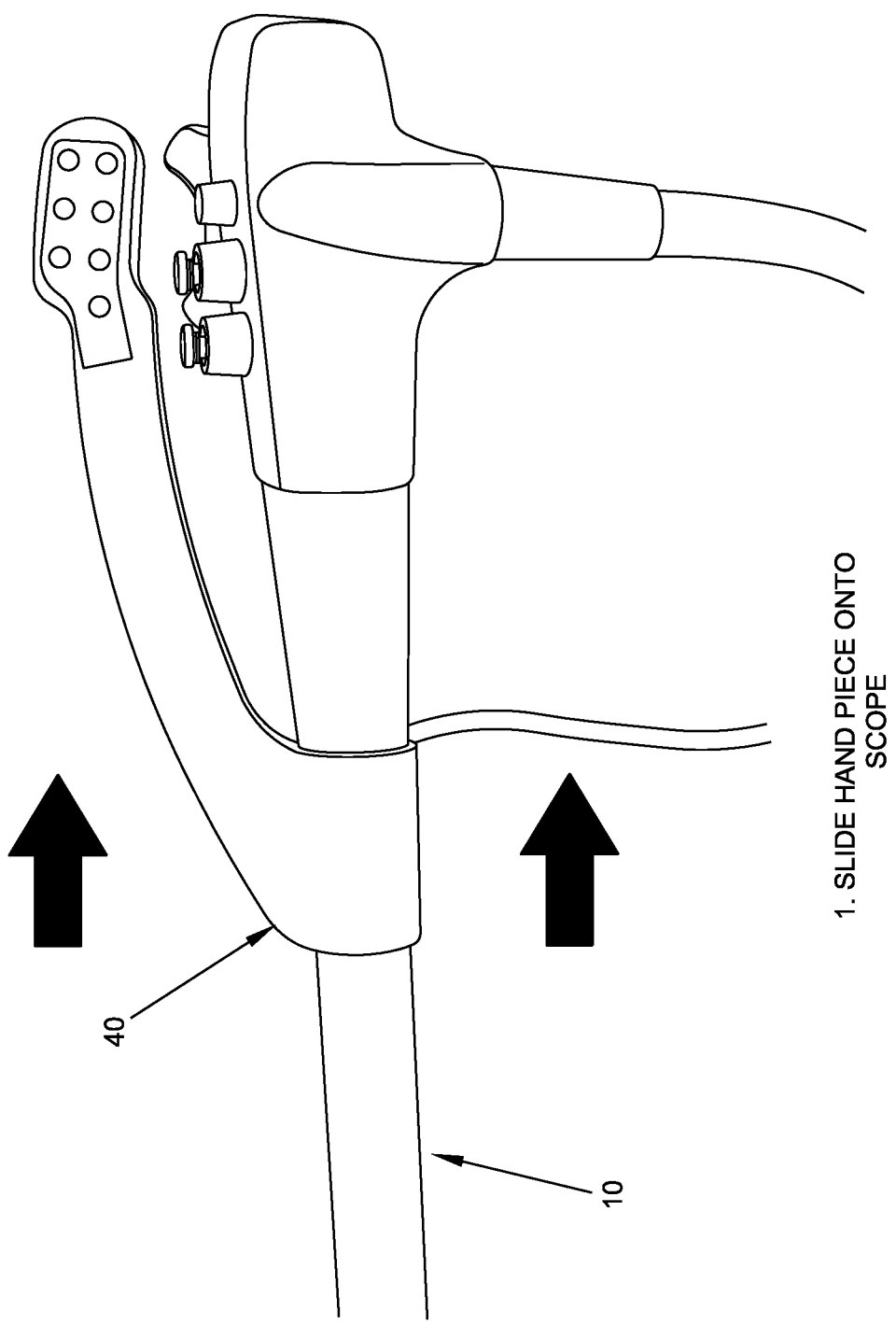
FIGS. 17-33 are schematic views illustrating a preferred method of using the present invention.
Figure 18:
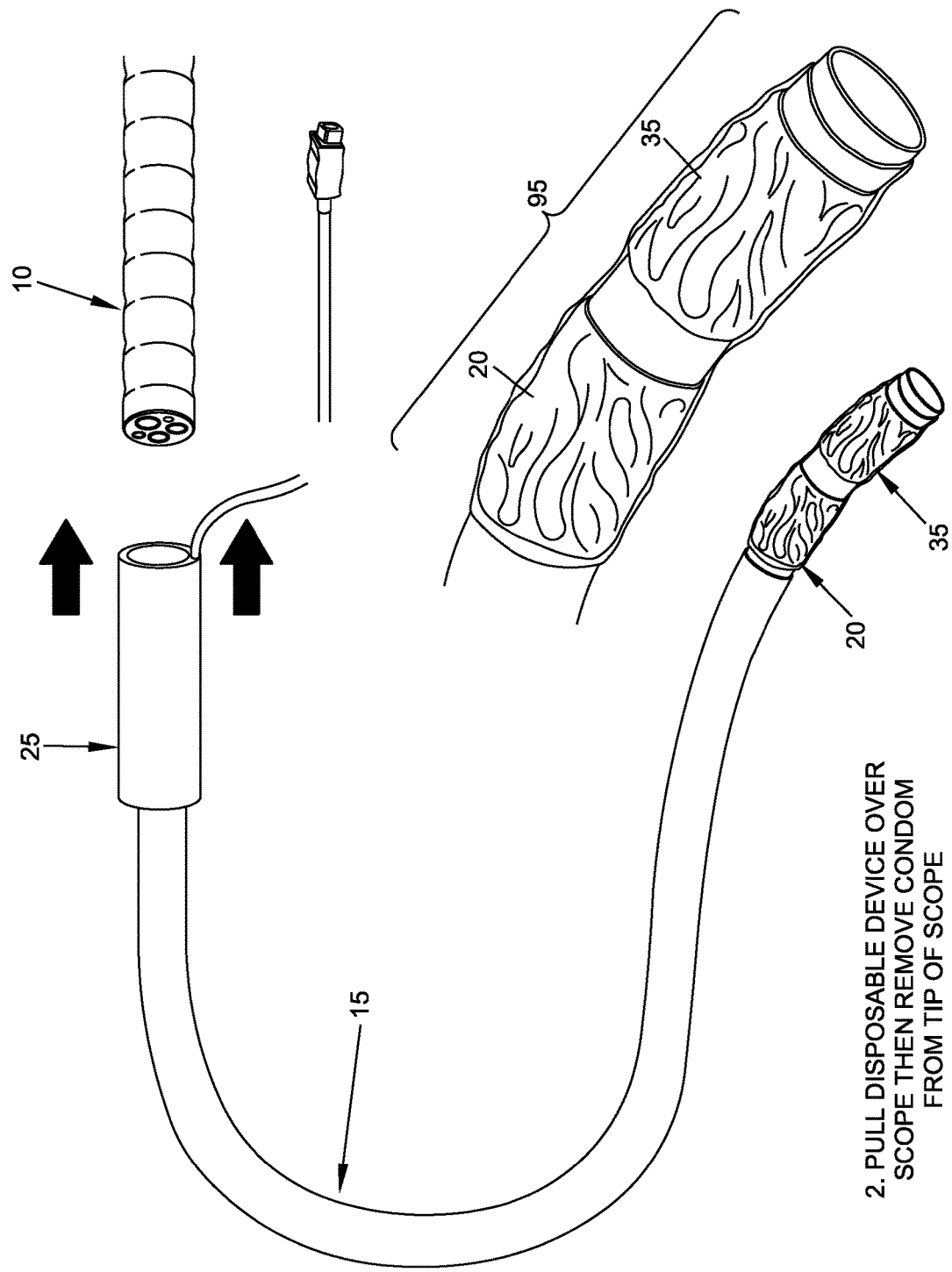
Figure 19:
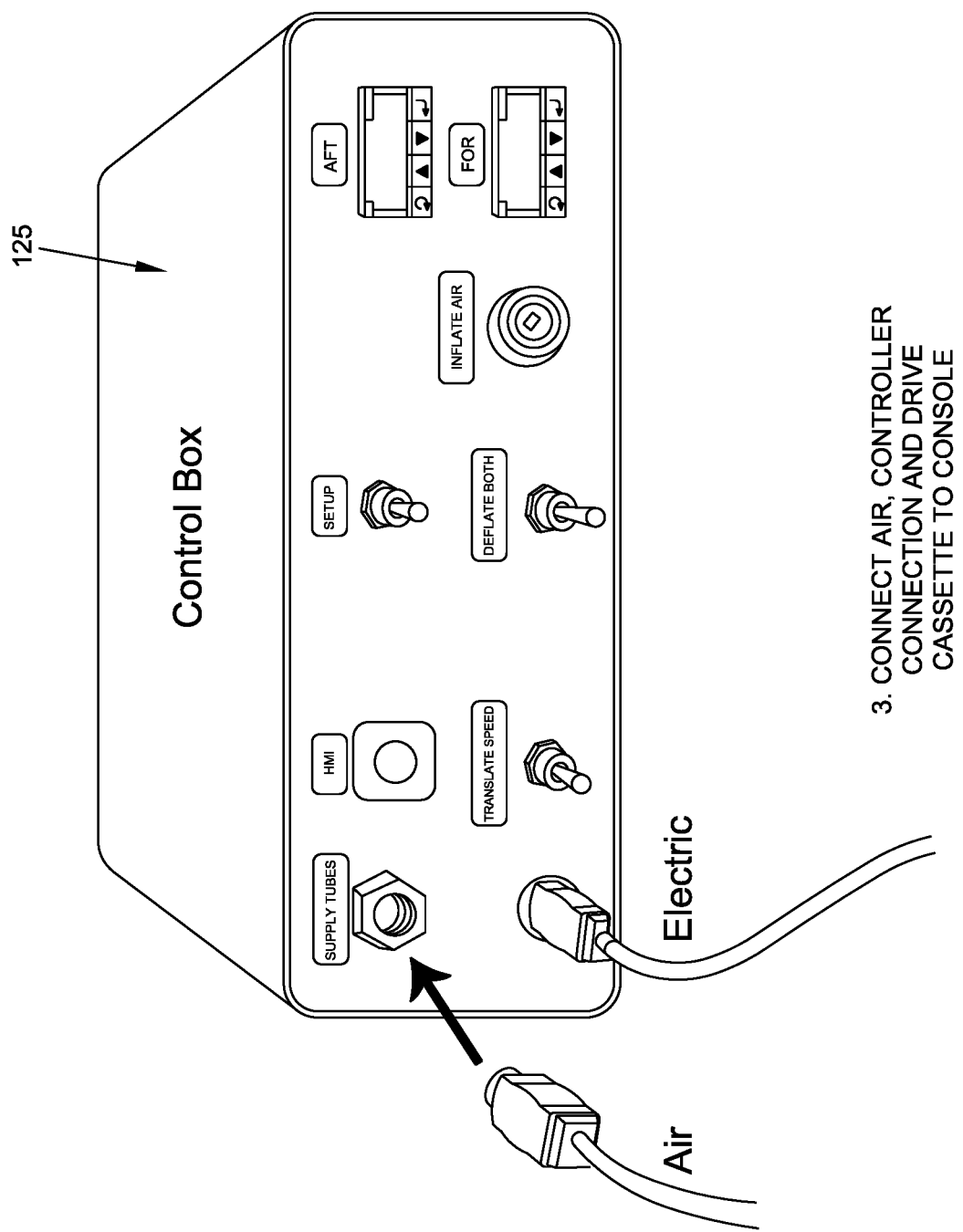
Figure 20:
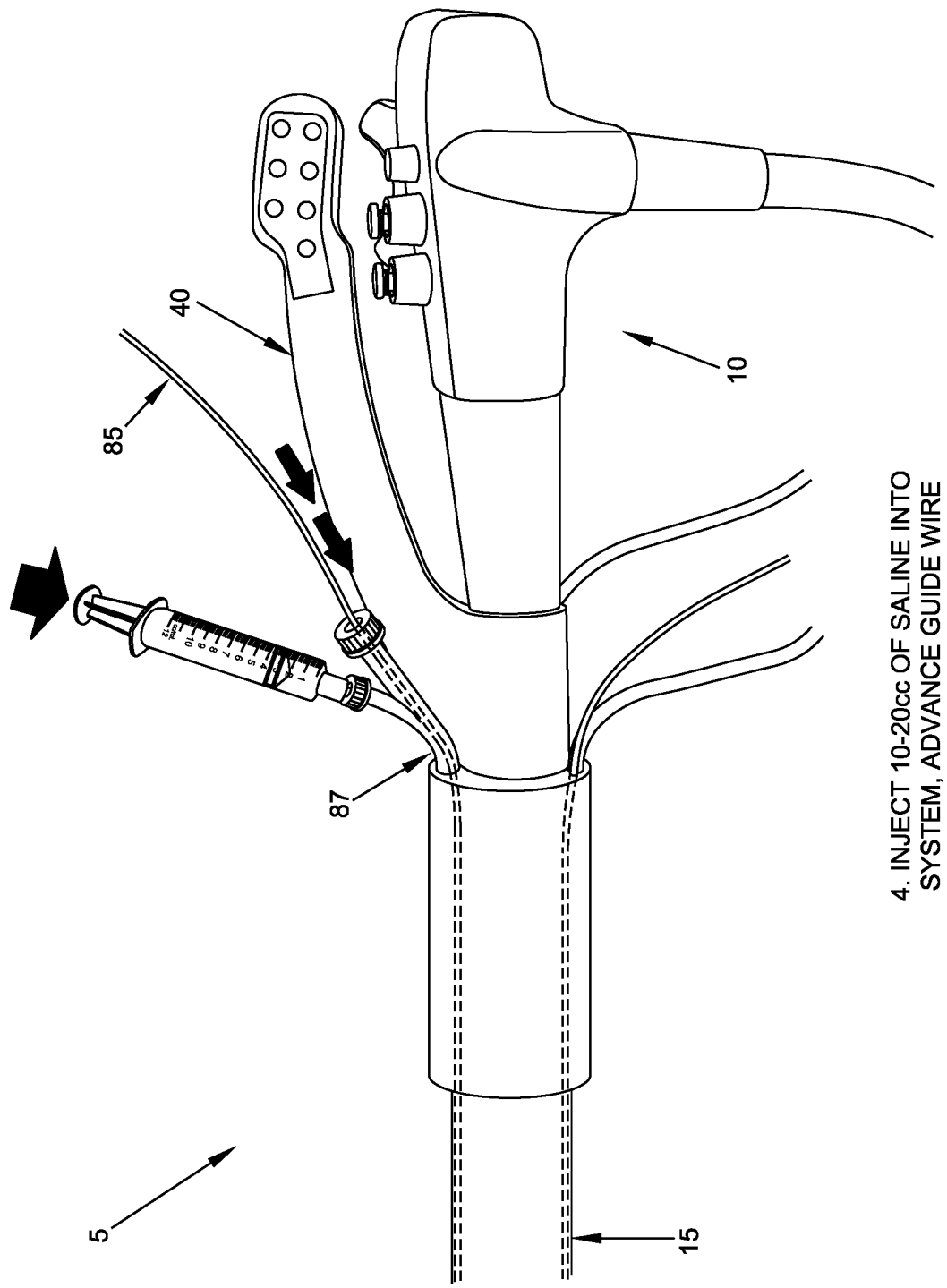

More particularly, in use, hand piece 40 is first mounted to endoscope 10 (FIG. 17), e.g., by pulling collar 115 over the shaft of the endoscope. Next, sleeve 15 is mounted to endoscope 10, i.e., by pulling handle 25 proximally onto the shaft of endoscope 10 (FIG. 18). Then, hand piece 40 has its electrical and fluid connections connected to controller 125 (FIG. 19), and retract line 60 and extend line 65 are connected to motorized drive system 130, e.g., by mounting eyelet 150 of retract line 60 on retract pull pin 135 and mounting eyelet 155 of extend line 65 on extend pull pin 140 (FIGS. 13-15). Next guidewire 85 is advanced through guidewire tube 87 and into support tube 30 until the distal tip of the guidewire is adjacent to the distal tip of endoscope 10 (FIG. 20). At this point, endoscope 10 and endoscopic stabilizing platform 5 are ready for insertion as a unit into the patent.

Figure 21:
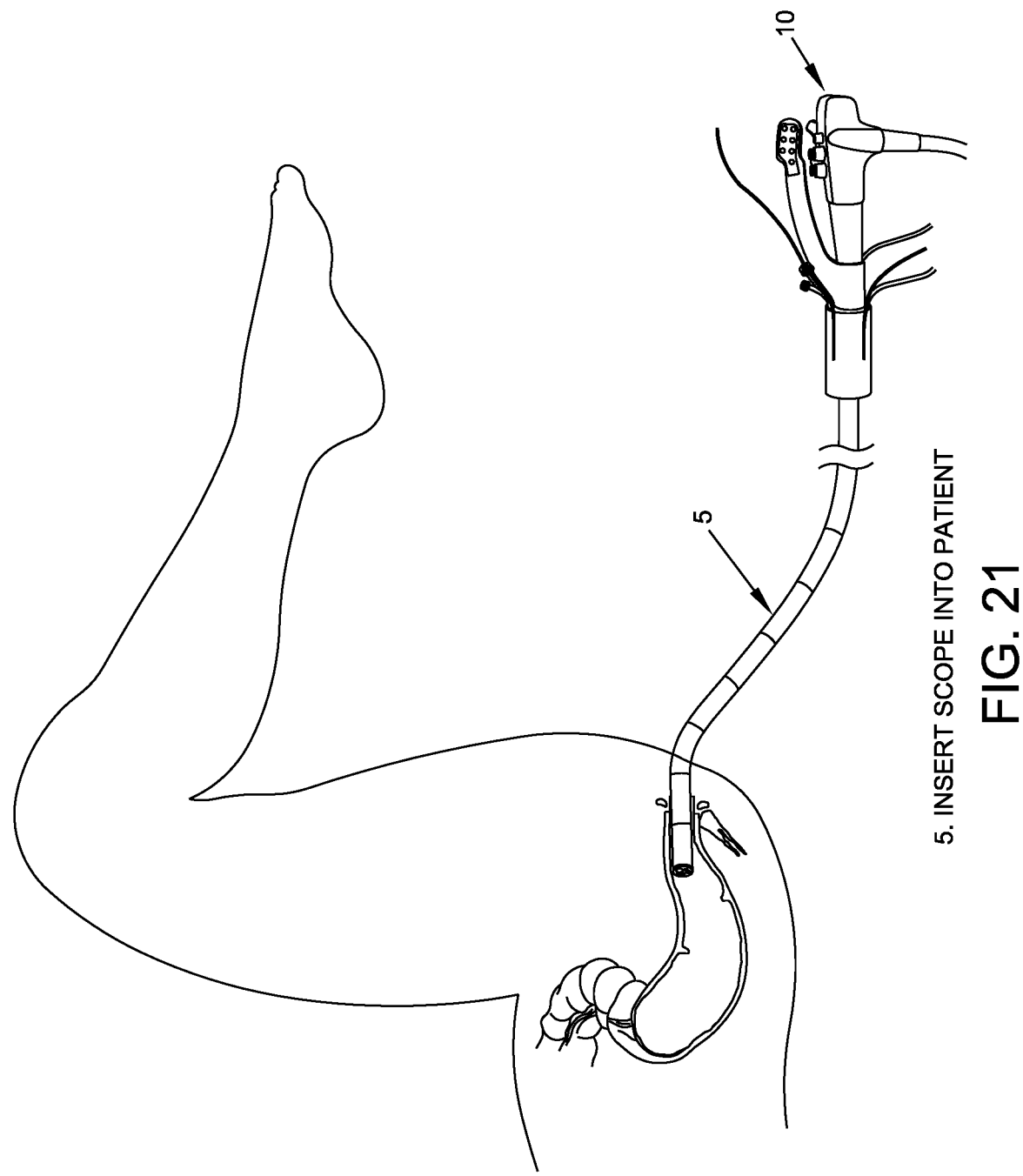
Figure 22:
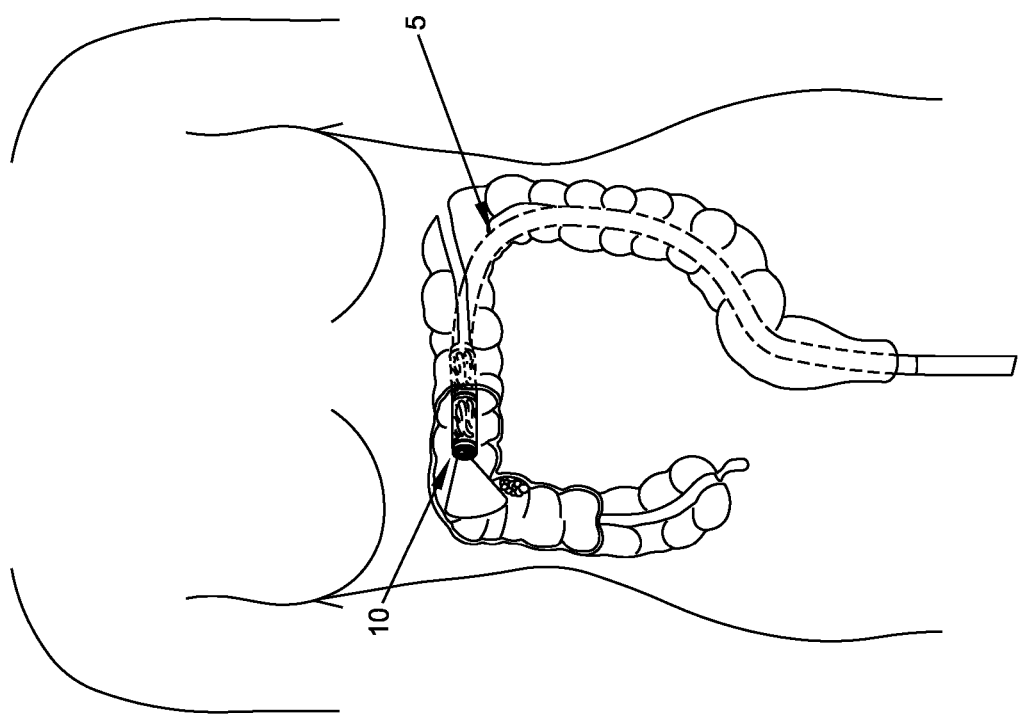
Figure 23:
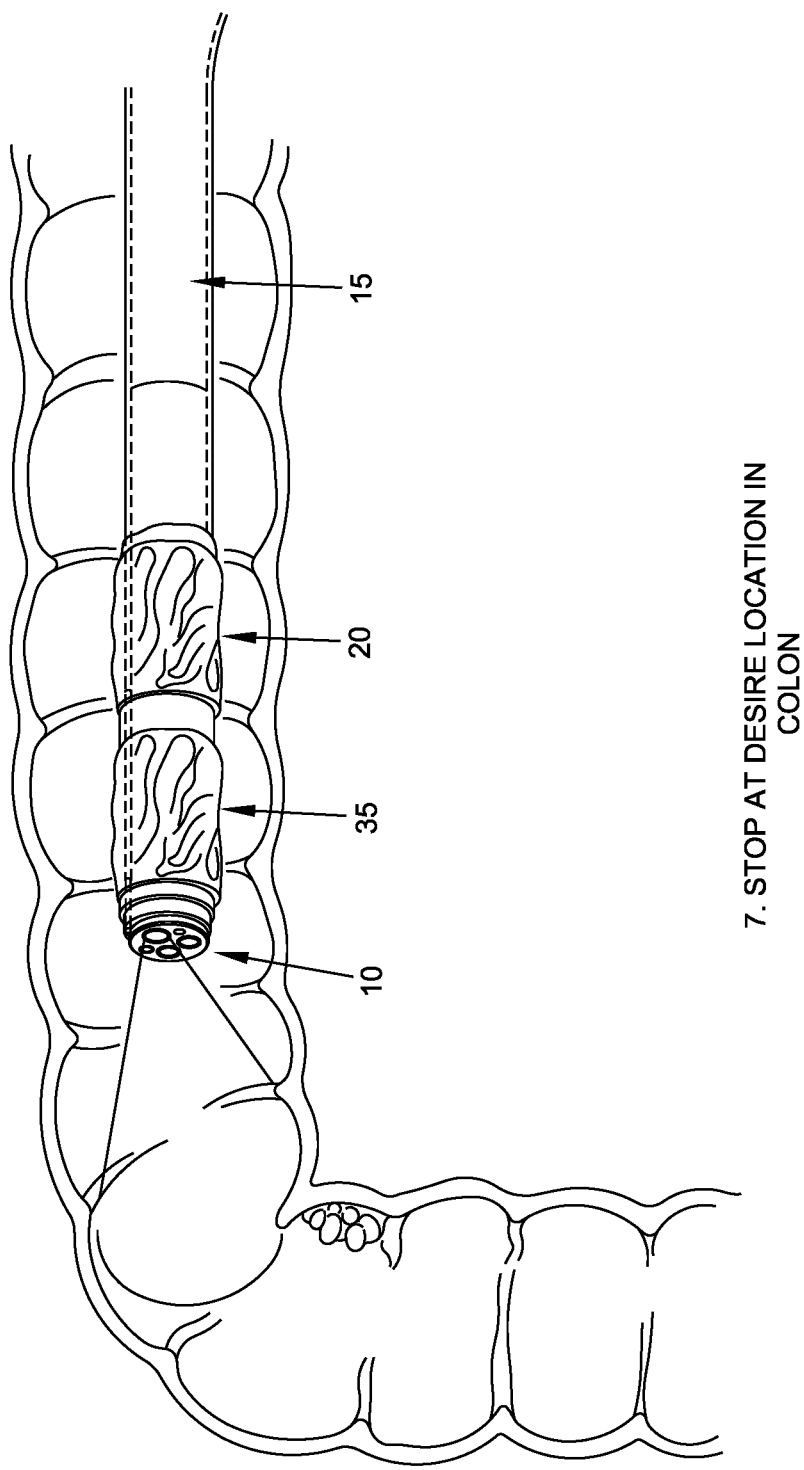

Looking next at FIG. 21, endoscope 10 and endoscopic stabilizing platform 5 are inserted as a unit into a body lumen and/or body cavity of the patient. By way of example but not limitation, endoscope 10 and endoscopic stabilizing platform 5 are inserted as a unit into the gastrointestinal (GI) tract of the patient. Endoscope 10 and endoscopic stabilizing platform 5 are advanced along the body lumen and/or body cavity to a desired location within the patient (FIGS. 22 and 23).

Figure 24:
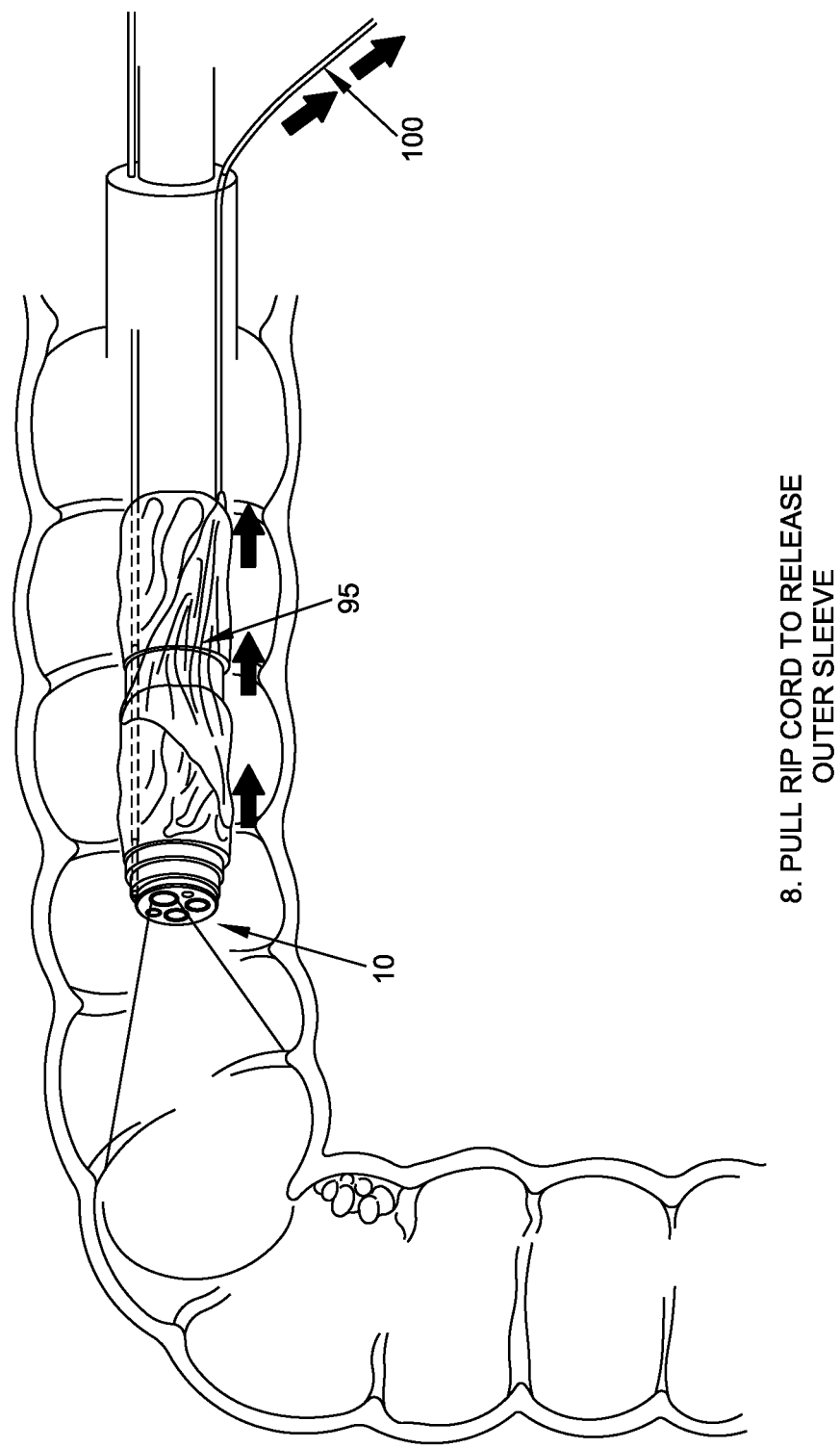

When endoscopic stabilizing platform 5 is to be used, rip cord 100 is pulled proximally so as to tear away rip sleeve 95 (FIG. 24). Then proximal balloon 20 is inflated so as to stabilize the endoscopic stabilizing platform (and hence endoscope 10) within the body lumen and/or body cavity.

Figure 25:
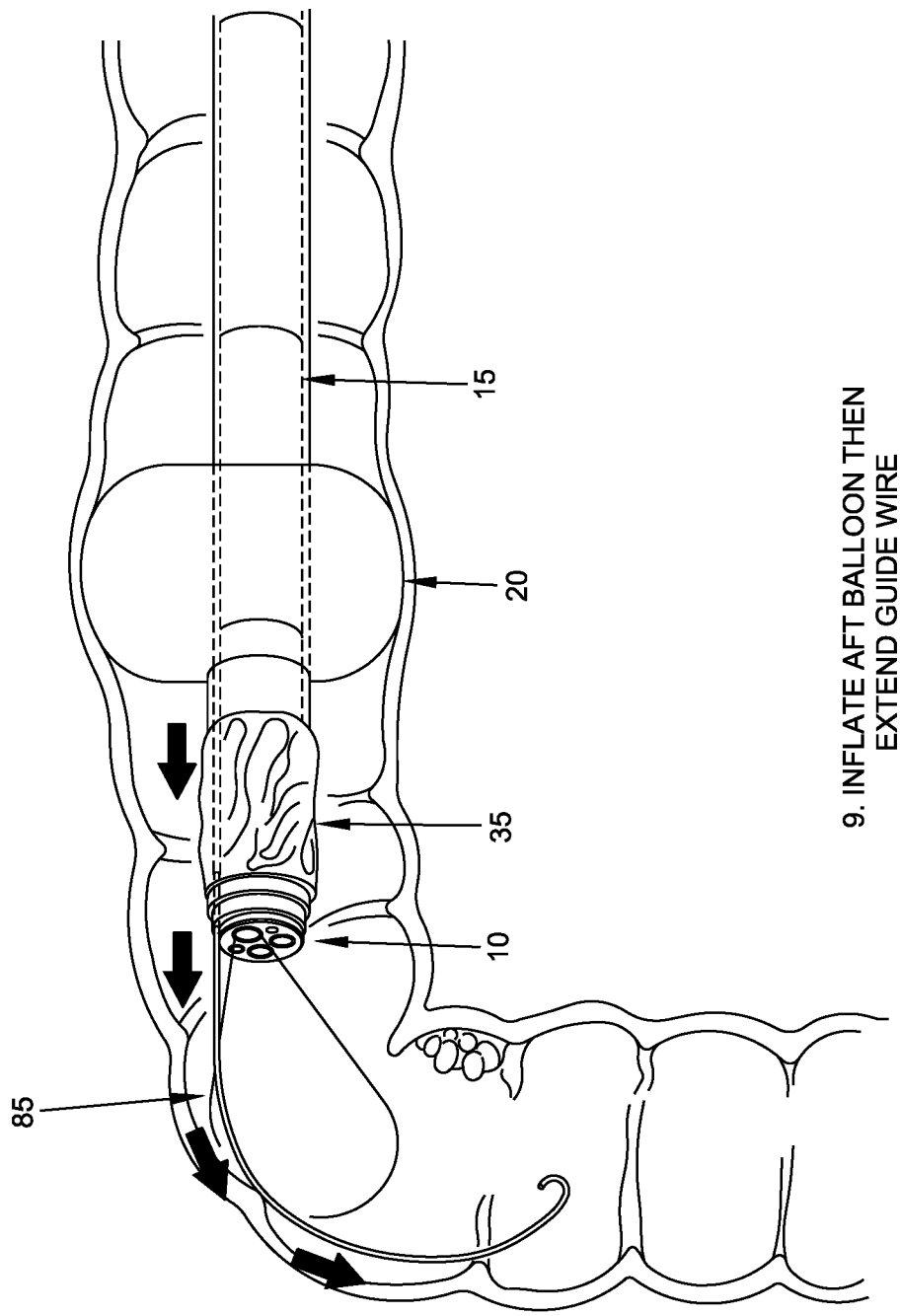

Next, guidewire 85 is advanced a further distance into the body lumen and/or body cavity (FIG. 25). In this respect it will be appreciated that the relatively small and relatively easily-steerable guidewire 85 will be relatively easy to direct to a desired location further down the body lumen and/or body passageway, particularly inasmuch as the guidewire may be advanced some or all of the way under direct visualization from endoscope 10. In this respect it will also be appreciated that inasmuch as the flexible portion of the endoscope resides distal to proximal balloon 20, the endoscope will be able to articulate distal to the balloon so as to facilitate visualization of the anatomy.

Figure 26:
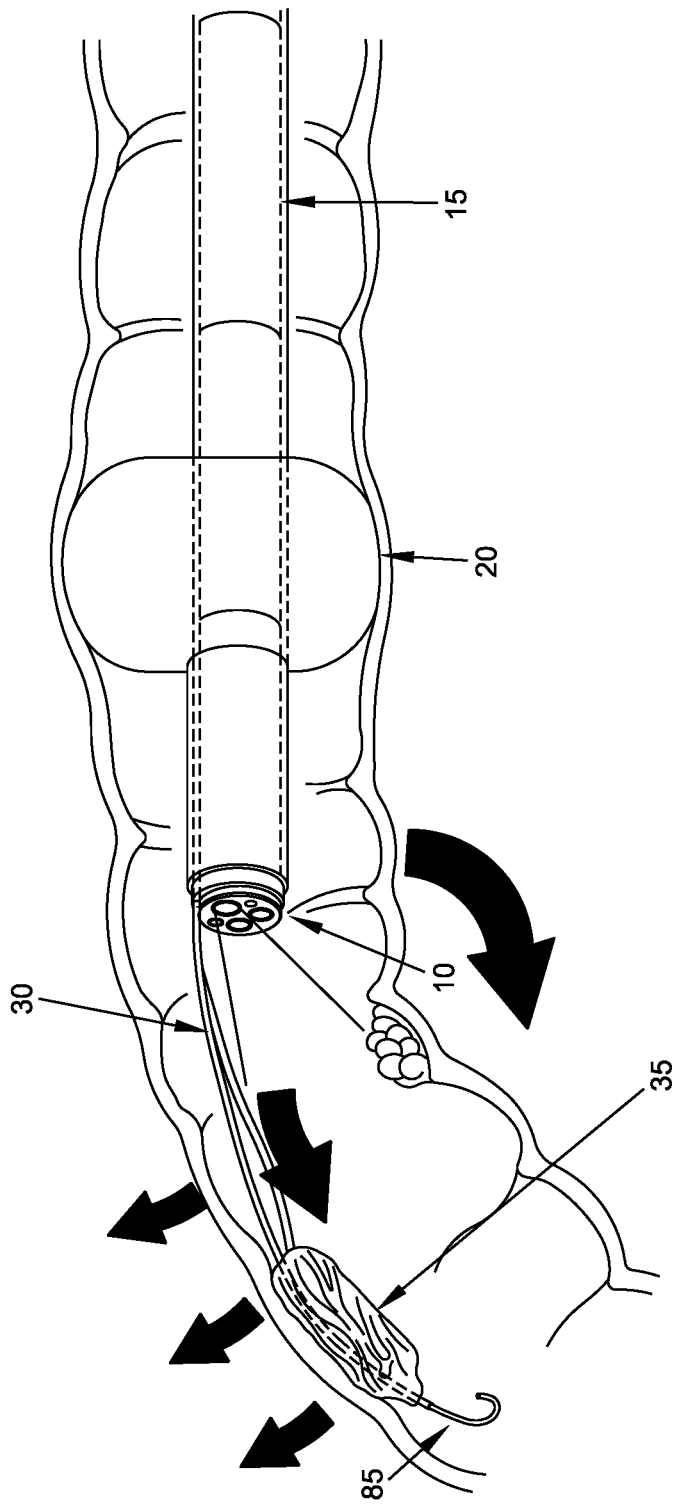

Next, pusher tube 30 is advanced distally along the guidewire (FIG. 26). Thus, guidewire 85 acts as guide for moving pusher tube 30, and hence distal balloon 35, distally relative to the endoscope 10.

Figure 27:
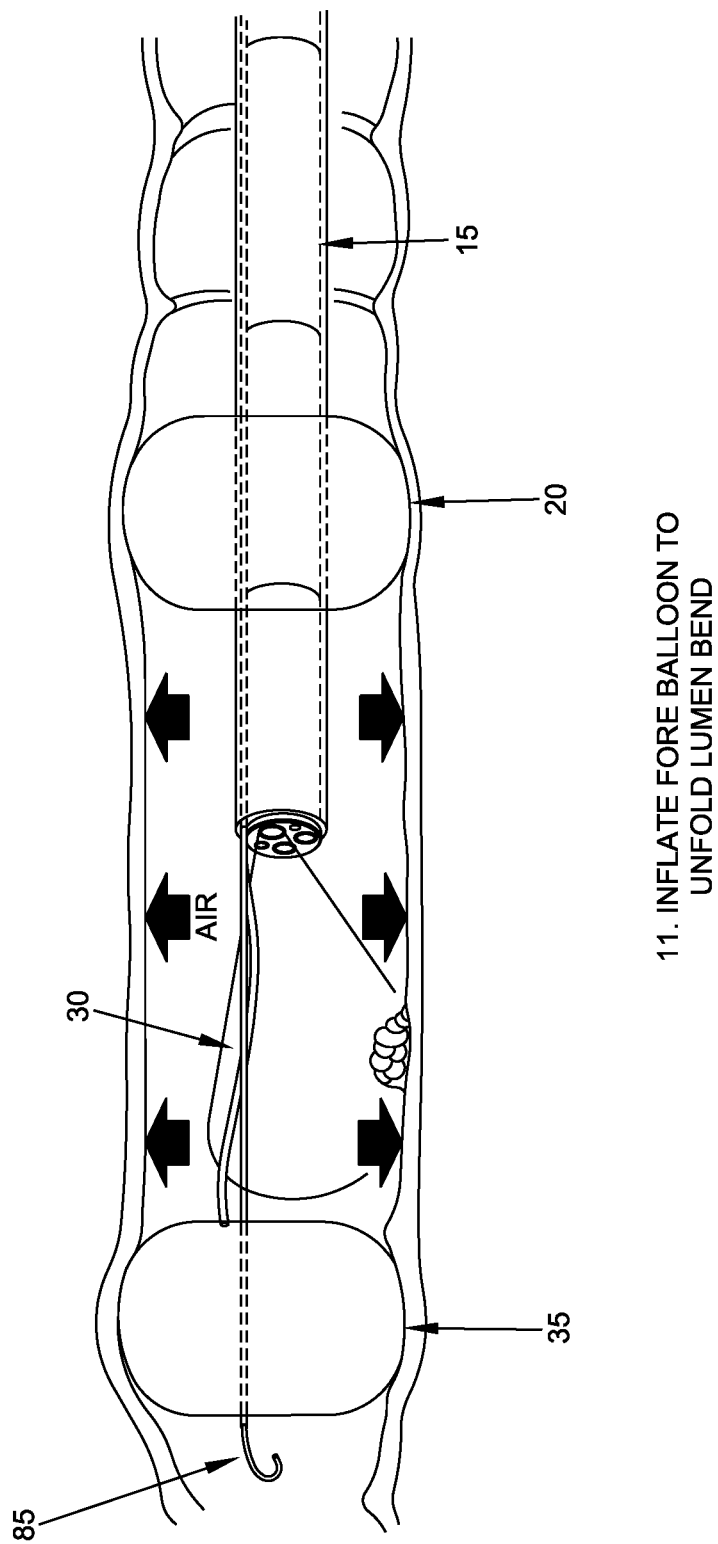

When pusher tube 30 has advanced distal balloon 35 to the desired position along guidewire 85, distal balloon 35 is inflated (FIG. 27) so as to secure distal balloon 35 to the anatomy. As distal balloon 35 is inflated, the inflated distal balloon 35 and the inflated proximal balloon 20 will cooperate with one another so as to stabilize, straighten, expand and/or flatten the side wall of the body lumen and/or body cavity so as to better present the side wall tissue for examination and/or treatment during an endoscopic procedure using endoscope 10. In this respect it will be appreciated that the inflated distal balloon 35 and the inflated proximal balloon 20 will together expand and tension the side wall of the body lumen and/or body cavity, and pusher tube 30 will tend to straighten the anatomy between the two inflated balloons. In this respect it will also be appreciated that once proximal balloon 20 and distal balloon 30 have both been inflated, they will together define a substantially closed region along the body lumen and/or body cavity (i.e., an isolated therapeutic zone) which can then be inflated with a fluid (e.g., air, $CO_2$, etc.). This fluid can significantly enhance visualization of the side wall of the body lumen and/or body cavity.

Figure 28:
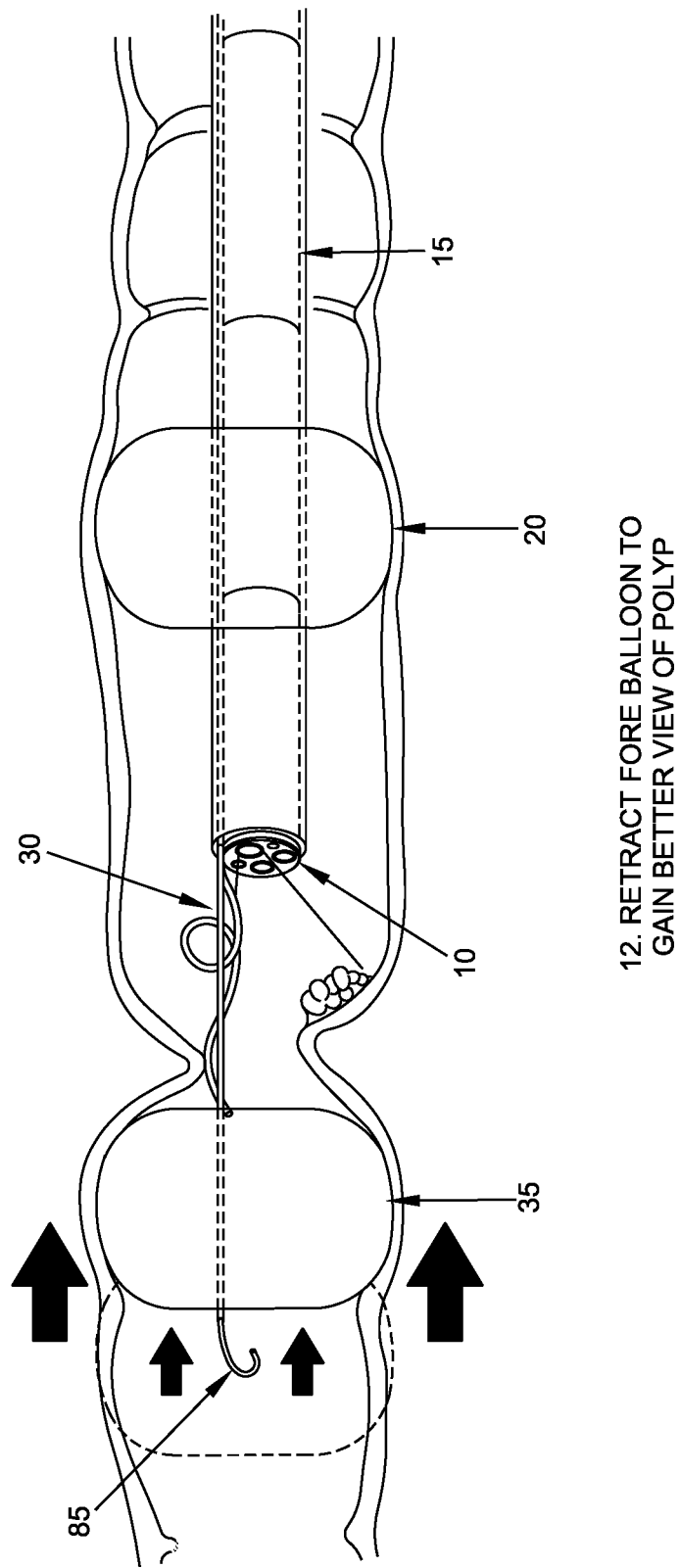

If desired, distal balloon 35 can be retracted toward proximal balloon 20, while remaining inflated, so as to move the anatomy and further improve visualization (see FIG. 28).

Figure 29:
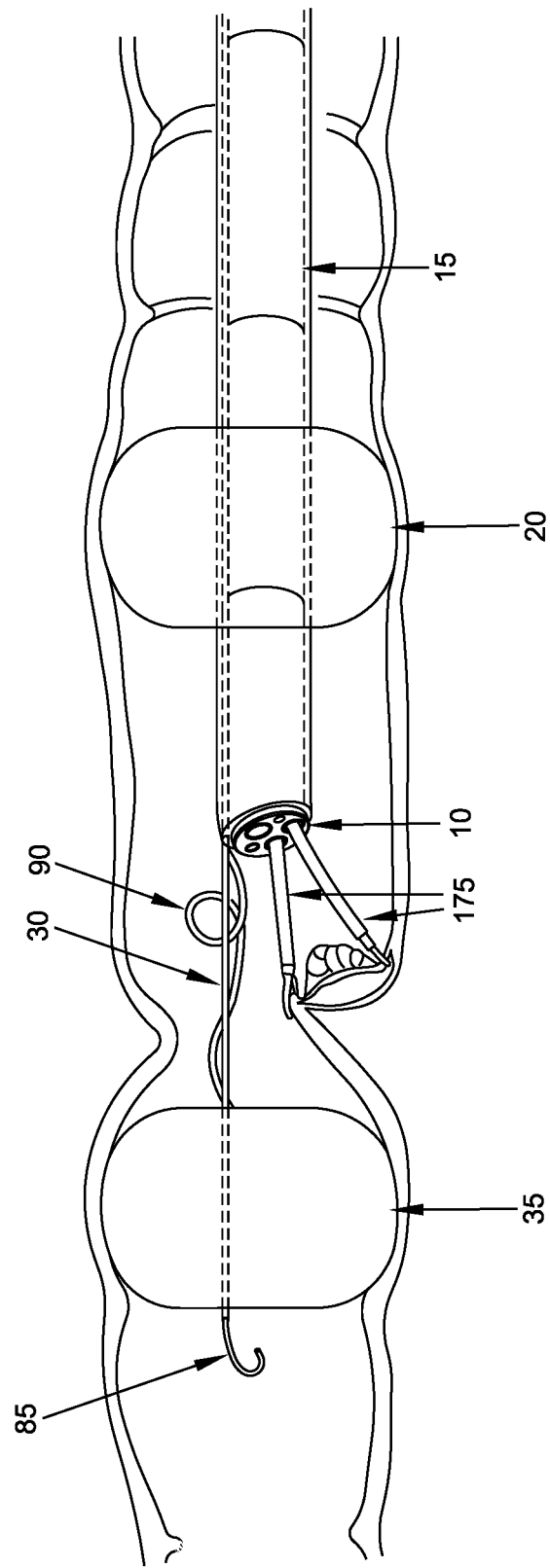

If desired, surgical tools 175 (FIG. 29) may be advanced through endoscope 10 so as to biopsy and/or treat the anatomy. It will be appreciated that such instruments will be advanced out of the distal end of the endoscope, which is highly stabilized relative to the anatomy via proximal balloon 20, so that the working ends of instruments 175 will also be highly stabilized relative to the anatomy. This is a significant advantage over the prior art practice of advancing tools out of the non-stabilized end of an endoscope.

Figure 30:
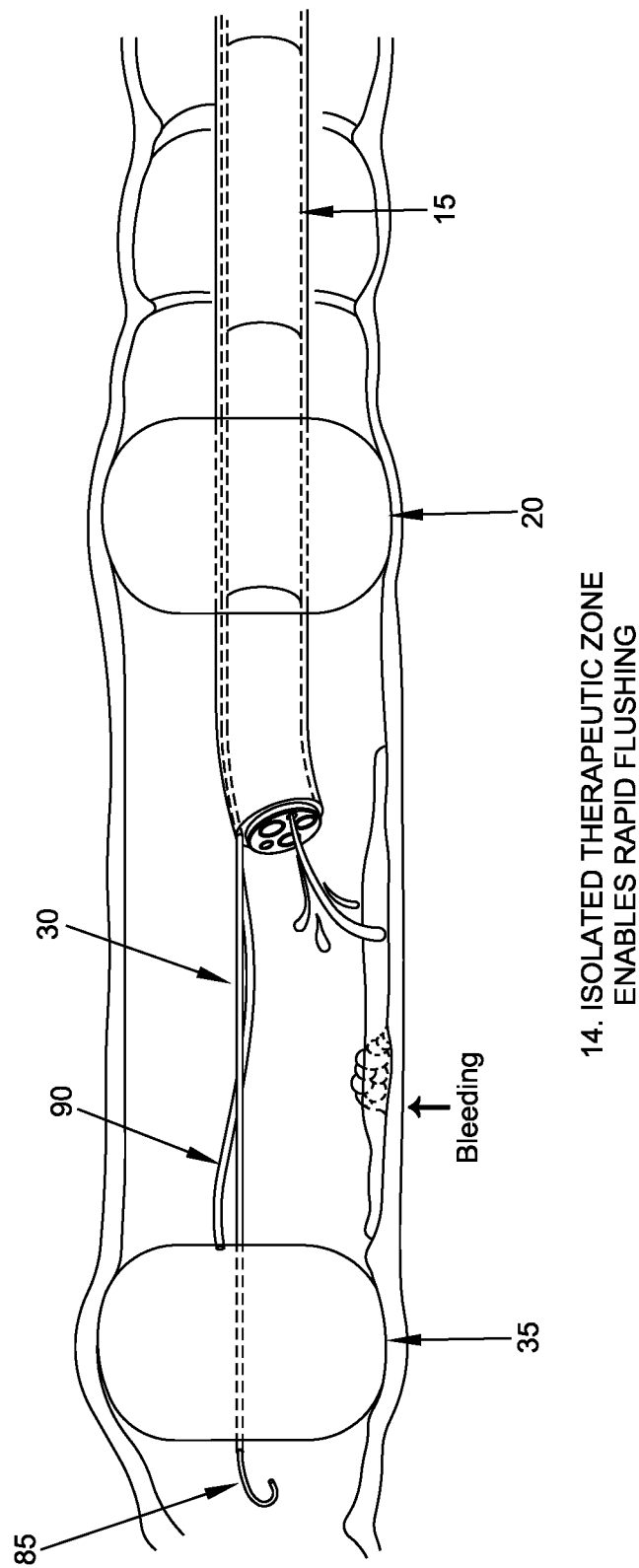
Figure 31:
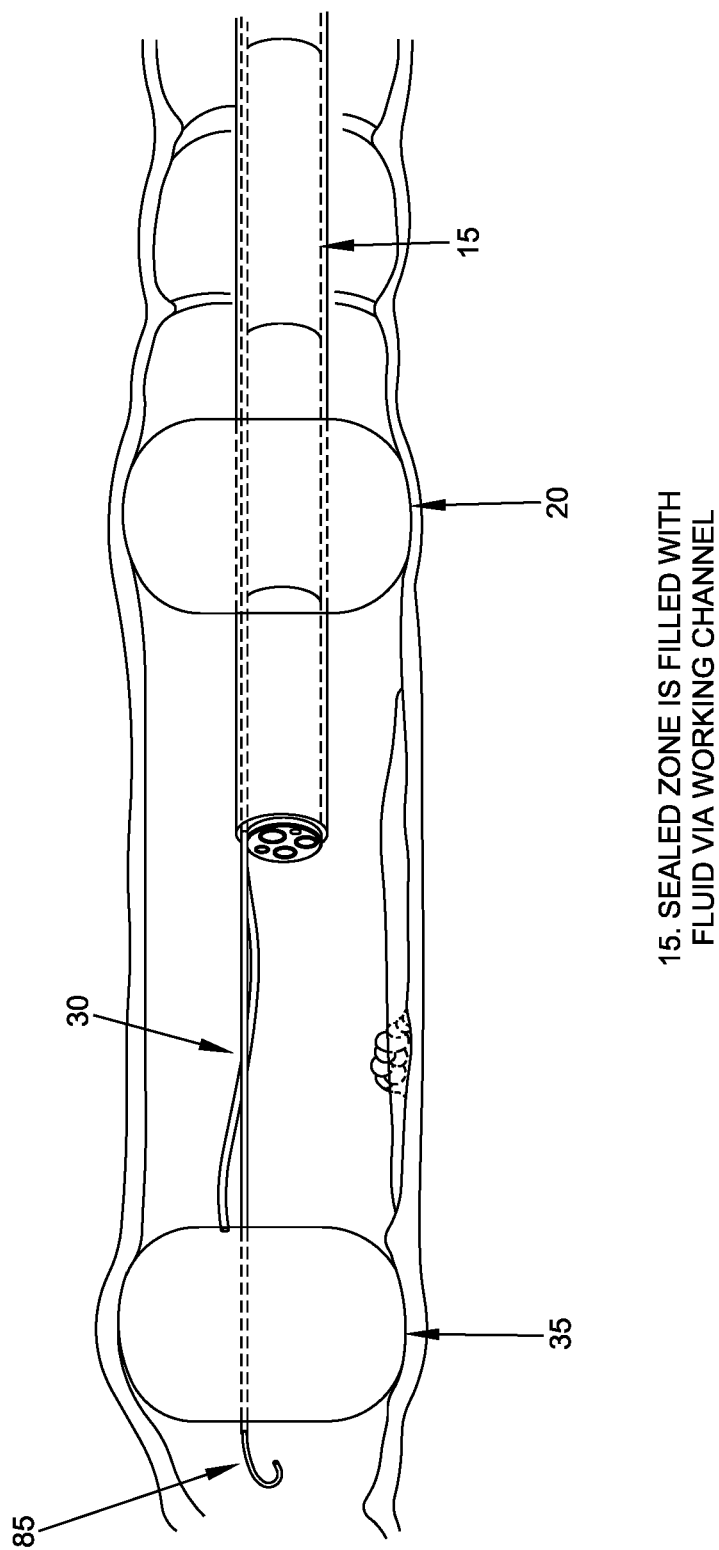
Figure 32:
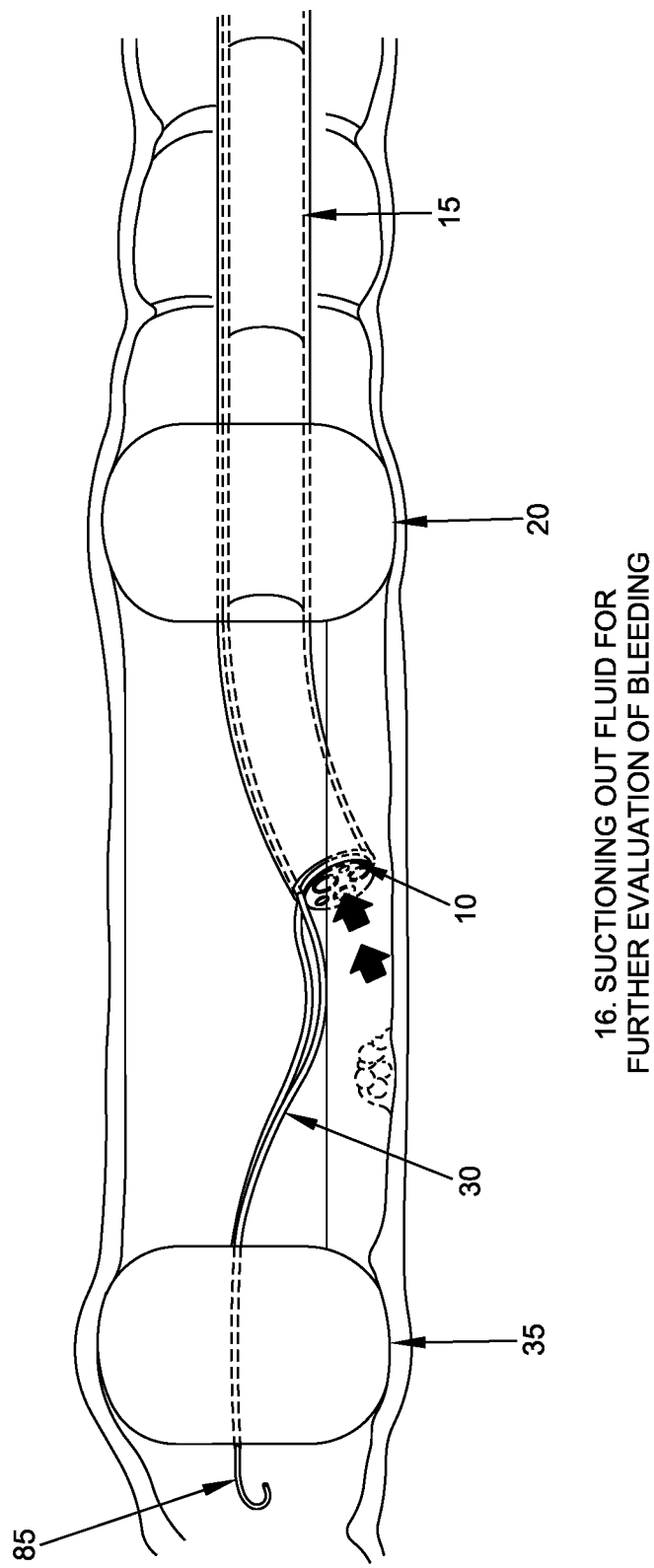

Furthermore, if bleeding were to obscure a tissue site, the isolated therapeutic zone permits rapid flushing of the anatomy and subsequent removal of the flushing liquid (see FIGS. 30-32).

Figure 33:
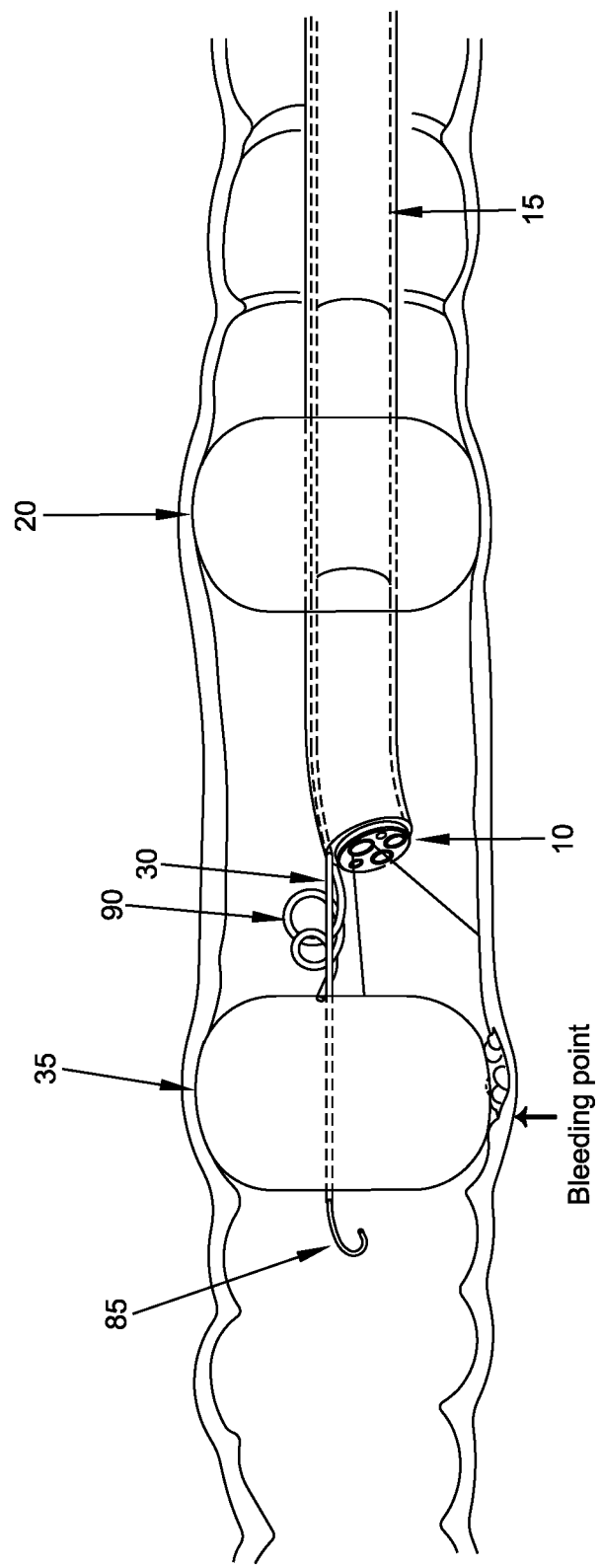
Figure 34:
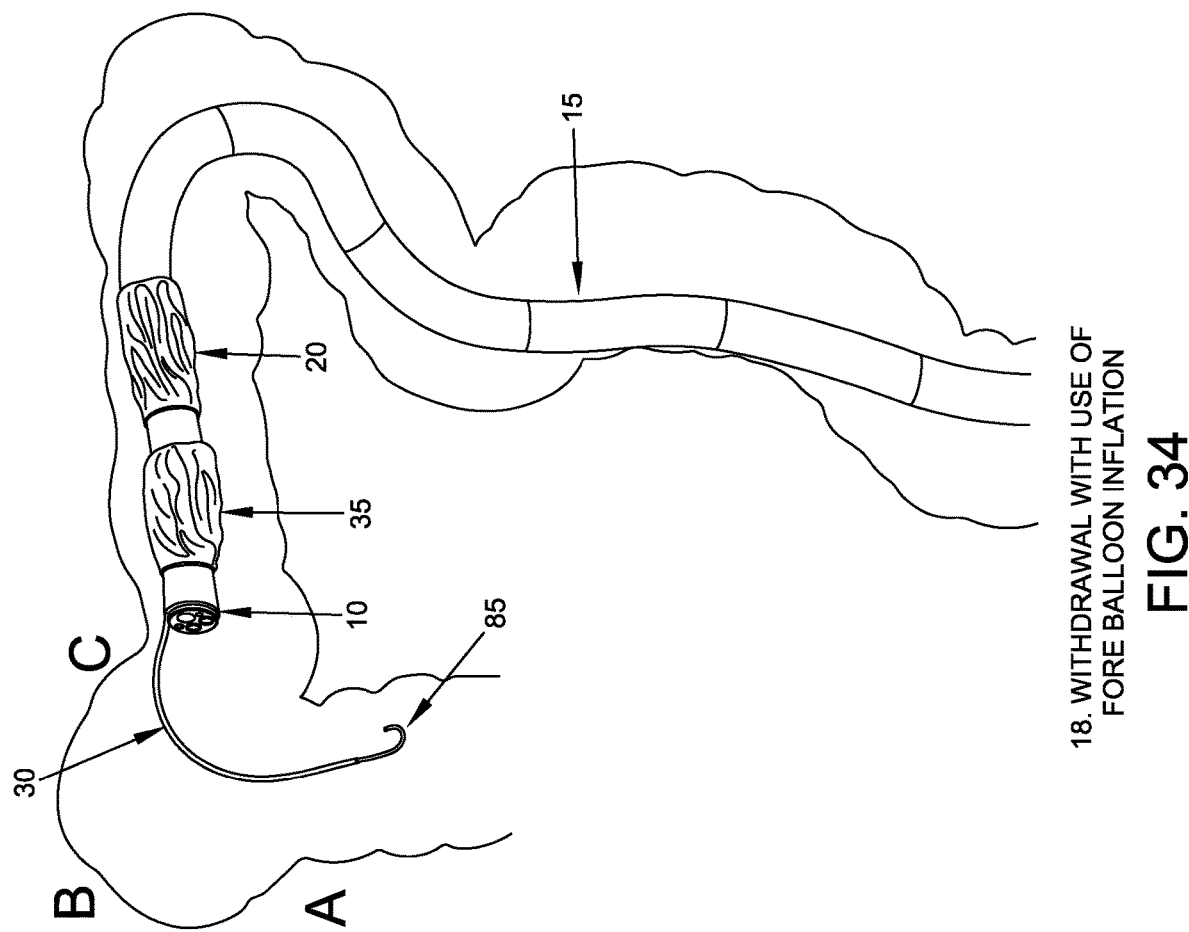
FIGS. 34-38 are schematic views showing an additional preferred method of using the present invention.

Also, if desired, the distal balloon 35 can be directed with high precision to the bleeding site via guidewire 85 and the guidewire-tracking pusher tube 30, whereupon distal balloon 35 may be used to apply topical pressure to the bleeding site in order to enhance bleeding control (see FIG. 33). This can be done under the visualization provided by endoscope 10.

Figure 35:
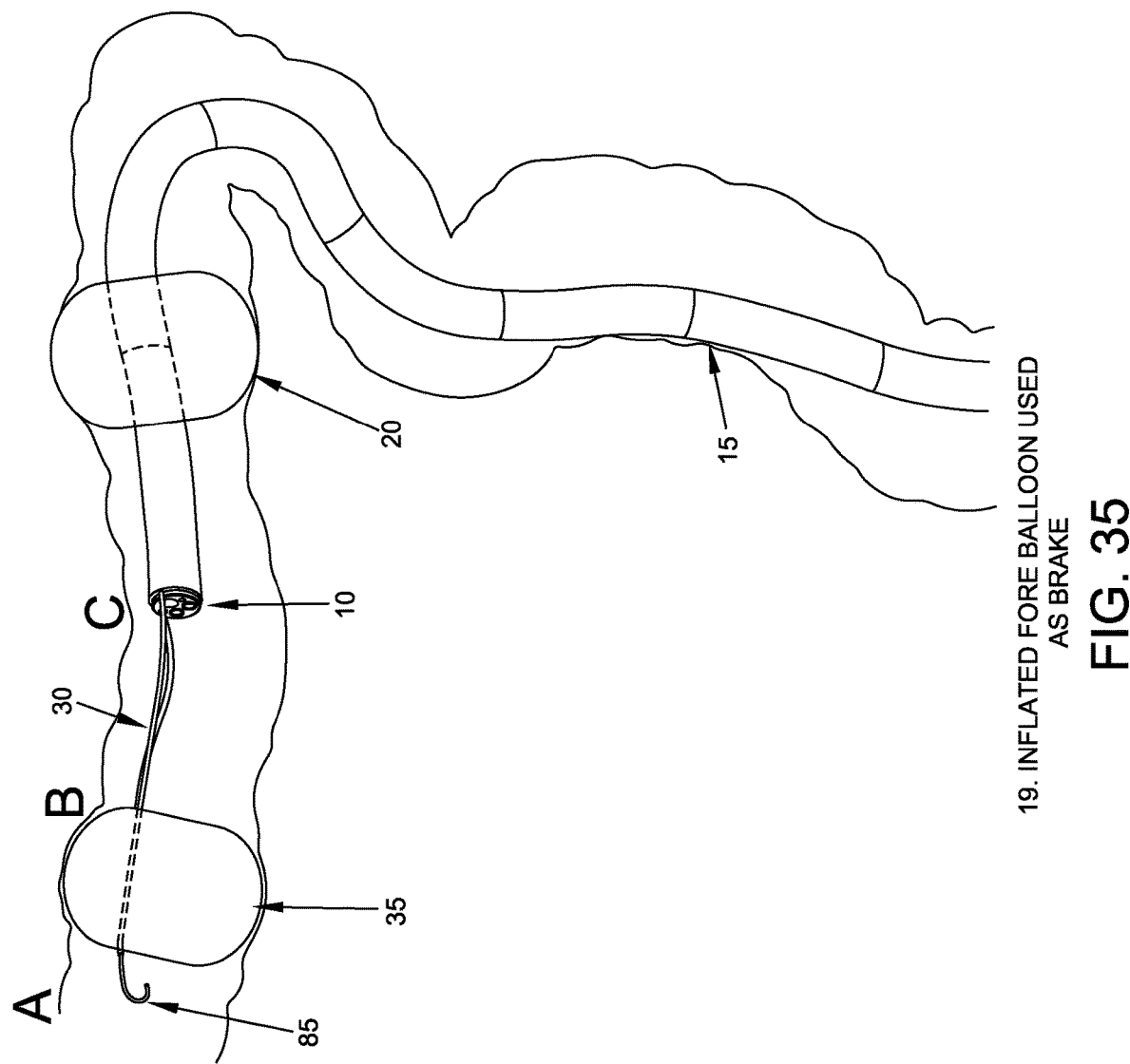
Figure 36:
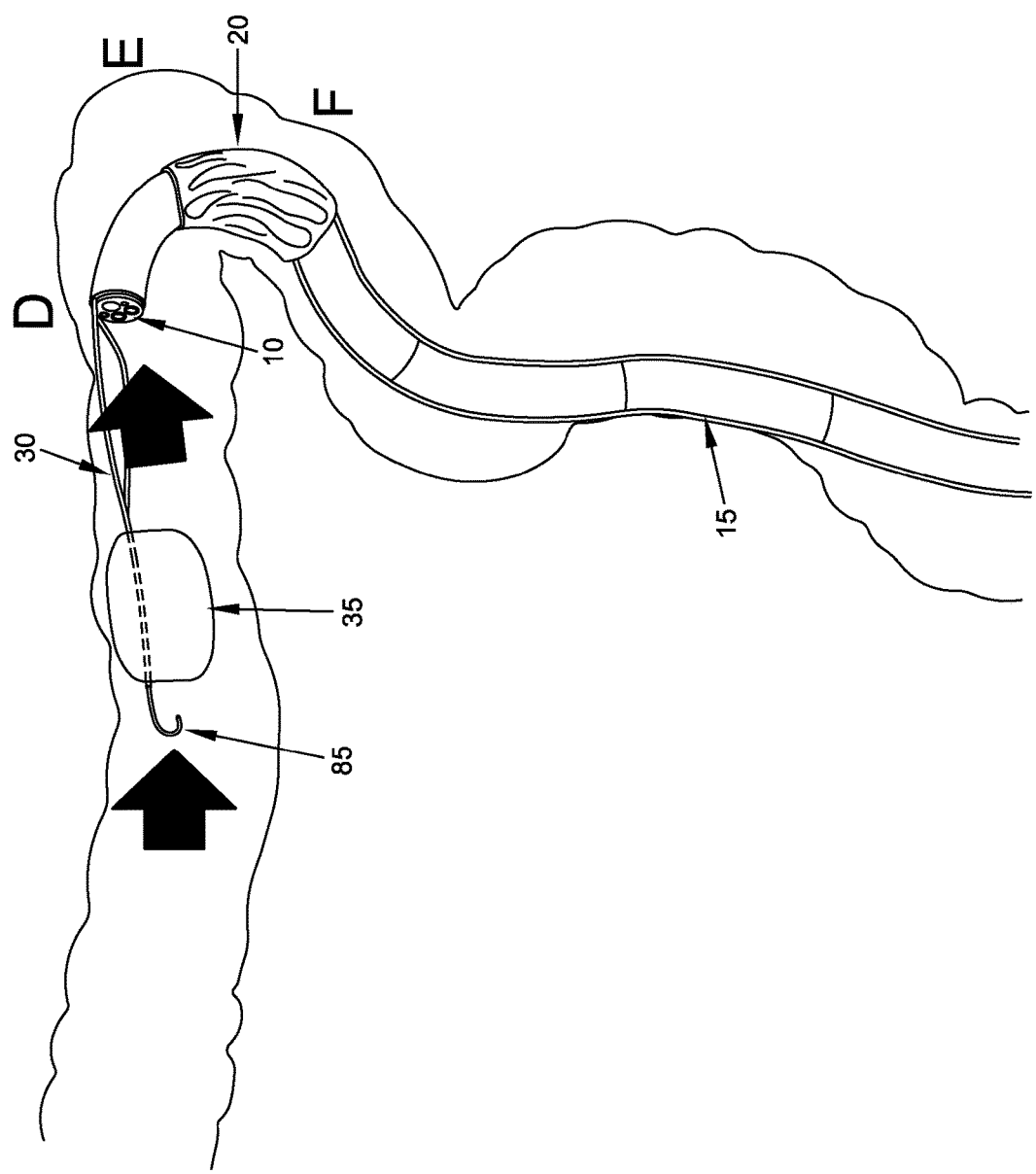
Figure 37:
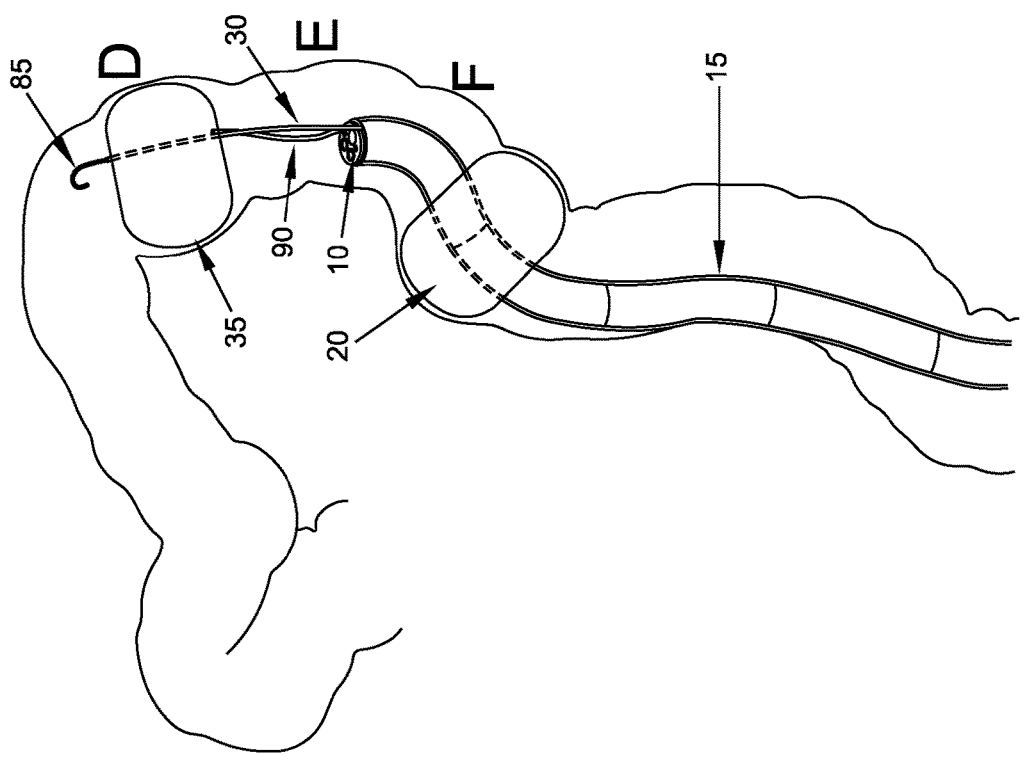
Figure 38:
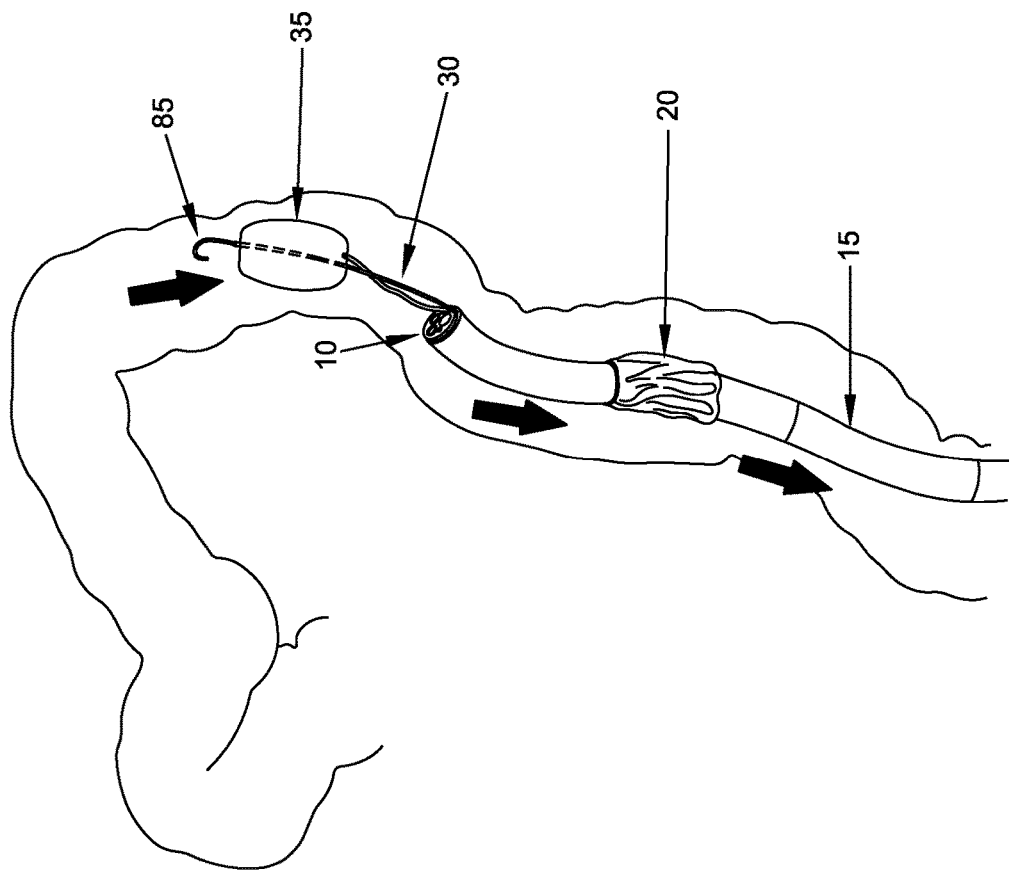

If desired, the distal balloon 35 may be used as a drag brake to control endoscope removal. More particularly, in this form of the invention, the endoscope 10 and the endoscopic stabilizing platform 5 are first advanced as a unit into the body lumen and/or body cavity until the tip of the endoscope is at the proper location, and then guidewire 85 is advanced distally. Next, proximal balloon 20 is inflated, pusher tube 30 is advanced distally along guidewire 85, and distal balloon 35 is inflated (FIG. 35). When the apparatus is to be withdrawn, proximal balloon 20 is deflated, distal balloon 35 is partially deflated, and then the endoscope is withdrawn proximally, dragging the semi-inflated distal balloon 35 along (FIG. 36), with distal balloon 35 acting as something of a brake as the endoscope is pulled proximally, thereby enabling a more controlled withdrawal of the endoscope and hence better visualization of the anatomy. If at some point it is desired, proximal balloon 20 and distal balloon 35 can be re-inflated, as shown in FIG. 37, with or without introduction of a fluid into the "isolated therapeutic zone" established between the two balloons, so as to stabilize, straighten, expand and/or flatten the anatomy. At the conclusion of the procedures, the system is withdrawn from the anatomy (FIG. 38).

It is also possible to use proximal balloon 20 as a brake when withdrawing the endoscope (and hence endoscopic stabilizing platform 5) from the anatomy, either alone or in combination with braking action from distal balloon 35.

APPLICATIONS

The novel endoscopic stabilizing platform of the present invention can be used in substantially any endoscopic procedure to facilitate the alignment and presentation of tissue during an endoscopic procedure and/or to, stabilize the working end of an endoscope (and/or other instruments advanced through the endoscope) relative to tissue during such a procedure.

The present invention is believed to have widest applications with respect to the gastrointestinal (GI) tract (e.g., large and small intestines, esophagus, stomach, etc.), which is generally characterized by frequent turns and which has a side wall characterized by numerous folds and disease processes located within these folds. However, the methods and apparatus of the present invention may also be used inside other body cavities (e.g., the cranium, thorax, abdomen, pelvis, nasal sinuses, bladder, etc.) and/or other tubular viscera (e.g., the vagina, ureter, fallopian tubes, urethra, blood vessels, bronchi, bile ducts, etc.).

Thus, for example, the novel endoscopic stabilizing platform of the present invention can be used in the performance of certain specialized endoscopic procedures including Natural Orifice Trans-Endoscopic Surgery (NOTES) procedures, as well as other complex endoscopic procedures which could involve endoscopic surgery.

MODIFICATIONS

While the present invention has been described in terms of certain exemplary preferred embodiments, it will be readily understood and appreciated by one of ordinary skill in the art that it is not so limited, and that many additions, deletions and modifications may be made to the preferred embodiments discussed above while remaining within the scope of the present invention.

What is claimed is:

1. A method for providing increased access to the side wall of a body lumen and/or body cavity while using an endoscope to visualize the side wall of the body lumen and/or body cavity, the endoscope having a distal end and a proximal end, wherein the proximal end of the endoscope comprises a handle, the method comprising:

providing an apparatus comprising:
a sleeve comprising a distal end, a proximal end and a lumen extending therebetween, the lumen being sized to receive the endoscope therein, and the sleeve being sized to extend over the endoscope from a location adjacent to the distal end of the endoscope to a location adjacent to the handle of the endoscope, wherein the sleeve comprises a channel having a distal end and a proximal end, wherein the distal end of the channel is disposed adjacent to the distal end of the sleeve and the proximal end of the channel is disposed adjacent to the proximal end of the sleeve;
a proximal balloon secured to the sleeve near the distal end of the sleeve;
a pusher tube slidably disposed in the channel of the sleeve so as to be movable relative to the sleeve, wherein the pusher tube comprises a distal end and a proximal end, with the distal end of the pusher tube being configured to extend out of the distal end of the channel, and with the proximal end of the pusher tube being configured to extend out the proximal end of the channel; and
a distal balloon secured to the distal end of the pusher tube;
sliding the sleeve over the endoscope so that the endoscope is disposed in the lumen of the sleeve and so that the distal end of the sleeve is disposed adjacent to the distal end of the endoscope and the proximal end of the sleeve is disposed adjacent to the handle of the endoscope;
positioning the endoscope and the apparatus in the body lumen and/or body cavity;
inflating the proximal balloon;
advancing the pusher tube relative to the sleeve so as to advance the distal balloon relative to the proximal balloon;
inflating the distal balloon so as to create a substantially fluidically sealed zone between the proximal balloon and the distal balloon; and
introducing fluid into the substantially fluidically sealed zone between the proximal balloon and the distal balloon.

2. A method according to claim 1 wherein the fluid introduced into the substantially fluidically sealed zone comprises air.

3. A method according to claim 1 wherein the fluid introduced into the substantially fluidically sealed zone comprises $CO_2$.

4. A method according to claim 1 wherein the fluid introduced into the substantially fluidically sealed zone comprises flushing liquid.

5. A method according to claim 4 further comprising removing flushing liquid from the substantially fluidically sealed zone.

6. A method according to claim 1 further comprising advancing a tool through the endoscope to the substantially fluidically sealed zone.

7. A method according to claim 6 further comprising using the tool to perform a procedure within the substantially fluidically sealed zone.

8. A method according to claim 7 wherein the procedure comprises a biopsy.

* * * * *